(12) United States Patent
Makowski

(10) Patent No.: US 7,920,316 B2
(45) Date of Patent: Apr. 5, 2011

(54) SYSTEMS AND METHODS FOR SENSORY STIMULATION

(75) Inventor: Natasha Makowski, Boston, MA (US)

(73) Assignee: ISPACE Artlab LLC, Boston, MA (US)

( * ) Notice: Subject to any disclaimer, the term of this patent is extended or adjusted under 35 U.S.C. 154(b) by 927 days.

(21) Appl. No.: 11/706,631

(22) Filed: Feb. 13, 2007

(65) Prior Publication Data

US 2007/0247700 A1 Oct. 25, 2007

Related U.S. Application Data

(60) Provisional application No. 60/794,304, filed on Apr. 21, 2006, provisional application No. 60/789,110, filed on Apr. 3, 2006, provisional application No. 60/772,685, filed on Feb. 13, 2006.

(51) Int. Cl.
*G02F 1/03* (2006.01)
*A61B 17/52* (2006.01)

(52) U.S. Cl. ............................................. 359/245; 600/9

(58) Field of Classification Search .................. 359/245, 359/296, 265–275; 349/19; 600/9, 310, 600/477; 607/88–94; 128/899
See application file for complete search history.

(56) References Cited

U.S. PATENT DOCUMENTS

| | | | |
|---|---|---|---|
| 6,091,184 A | 7/2000 | De Vries et al. | |
| 6,352,748 B1 | 3/2002 | Aylward et al. | |
| 6,663,659 B2 * | 12/2003 | McDaniel | 607/88 |
| 6,970,155 B2 | 11/2005 | Cabrera | |
| 2004/0066363 A1 | 4/2004 | Yamano et al. | |
| 2004/0246413 A1 | 12/2004 | Stephenson et al. | |
| 2004/0260367 A1 * | 12/2004 | De Taboada et al. | 607/88 |
| 2005/0259211 A1 | 11/2005 | Stephenson et al. | |

FOREIGN PATENT DOCUMENTS

WO WO-01/06816 A1 1/2001

* cited by examiner

*Primary Examiner* — Scott J Sugarman
*Assistant Examiner* — Tuyen Q Tra
(74) *Attorney, Agent, or Firm* — Kuta IP Law LLC; Christine M. Kuta

(57) ABSTRACT

The invention relates generally to cognitive stimulation apparatuses and systems, and methods of manufacturing the same. In certain exemplary implementations the invention provides an at least partially transparent, pliable gel having an optical property, such as brightness or color, and a circuit for delivering electromagnetic radiation to the gel to modify the optical property. Under certain conditions, modifying the optical property can stimulate a user's visual and other senses to help improve cognitive development and functionality.

44 Claims, 15 Drawing Sheets

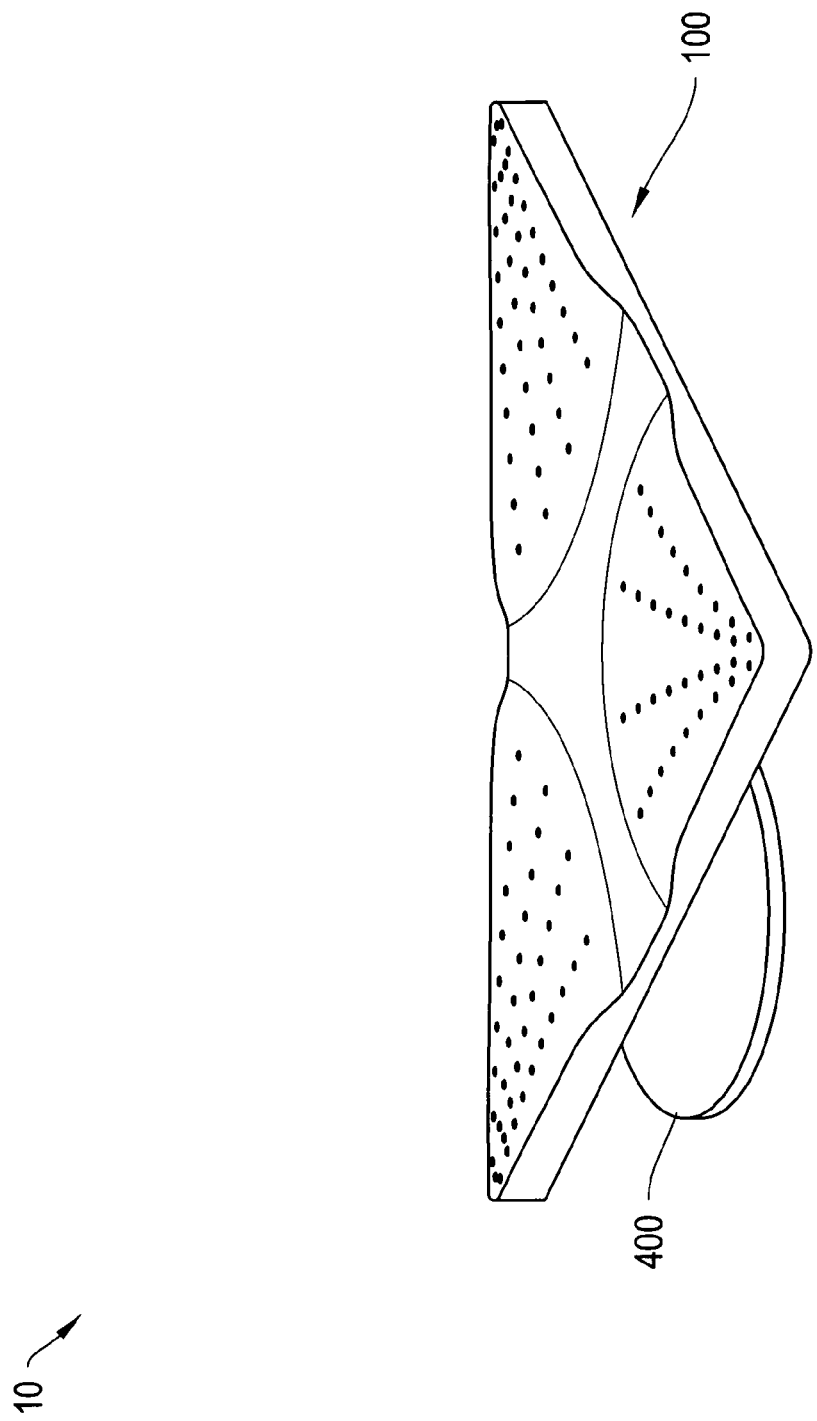

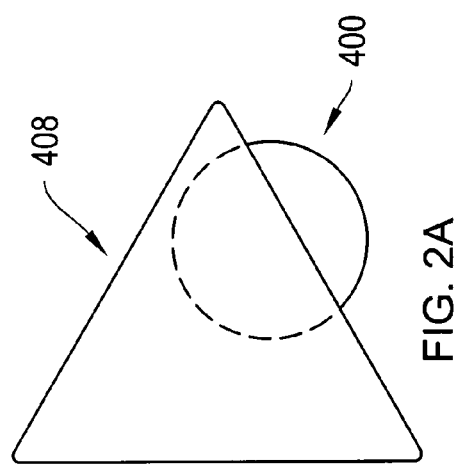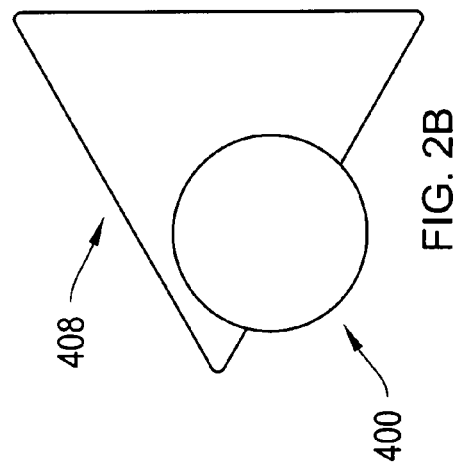
FIG. 2A
FIG. 2B

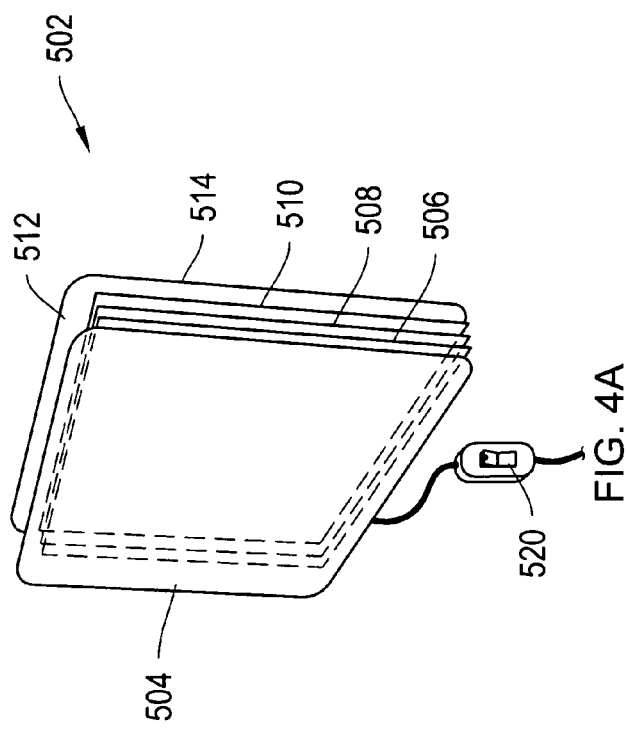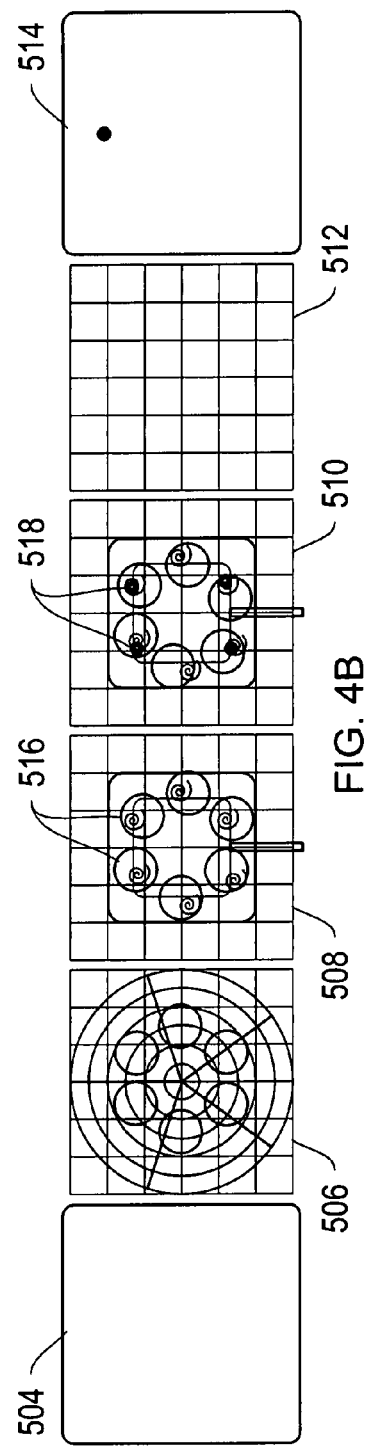

SYSTEMS AND METHODS FOR SENSORY STIMULATION

CROSS-REFERENCE RELATED APPLICATIONS

This application claims priority to and the benefit of U.S. Provisional Patent Application Ser. No. 60/772,685, filed on Feb. 13, 2006 and entitled "Methods and Systems of Customized Surfaces," U.S. Provisional Patent Application Ser. No. 60/789,110, filed on Apr. 3, 2006 and entitled "Systems and Methods for Preparing a Customized Surface," and U.S. Provisional Patent Application Ser. No. 60/794,304, filed on Apr. 21, 2006 and entitled "Systems and Methods for Preparing a Customized Surface," the entire contents of each of which are incorporated herein by reference.

BACKGROUND

Many tools are available to assist cognitive development and stimulation. From colorful building blocks to complex computer software, these tools help to improve sensory responses and assist general mental development. A set of such tools was developed for children by Friedrich Froebel in 1837 in Bad Blankenburg Germany. His tools included special materials such as wooden bricks having many different shapes, wooden sticks of different sizes and yarn balls having different textures and colors. These tools can generally be used in constructive exercises such as stacking a set of bricks to form larger shapes and touching different balls of yarn to identify textures. Children practicing these constructive exercises can improve their sensory responses.

Many commonly available sensory and cognitive development tools are suboptimal in that they require the user to handle a large number of heavy objects to develop tactile senses and improve general cognitive function. For example, to demonstrate the variation of textures in the Froebel system, a number of separate objects are needed and these objects are generally required to be made from different materials. Thus, to implement a Froebel based system, a child would be required to obtain a number of separate sensory development tools, each having different textures. Such a solution often proves to be quite expensive, which could limit the child's access to varied textured developmental tools.

There is a need for improved textured surfaces, and methods of manufacture thereof, that can assist tactile development, shape recognition, color study, material discovery and other cognitive development processes.

SUMMARY

The invention relates generally to cognitive stimulation systems and methods of manufacturing the same. In one aspect, the invention is directed to a sensory stimulation apparatus. The apparatus includes an at least partially transparent pliable, injection moldable material having an optical property, and a circuit for delivering electromagnetic radiation to the injection moldable material to modify the optical property, such as the brightness, color or other optical properties. Under certain conditions, modifying the optical property can stimulate a user's visual and other senses to help improve cognitive development. The electromagnetic radiation used to modify the optical property may include waves in the visible spectrum and/or the ultraviolet spectrum.

In certain embodiments, the injection moldable material is a gel. The gel may include polymeric materials such as thermoset elastomers. In certain embodiments, the gel includes at least one smart substance having an optical property. The smart substance may include a photochromic compound, a halochromic compound, a thermochromic compound and/or an electrochromic compound.

In certain embodiments, the apparatus has one or more interactive layers in interoperation with the gel. In certain embodiments, the one or more interactive layers include one or more of a backlight layer, a touch sensitive layer and a display layer. In such embodiments, the apparatus may also have a processing module for measuring and controlling the operation of the one or more interactive layers. The one or more interactive layers may include electronic components.

The circuit of the apparatus is configured to provide electromagnetic radiation to the gel. In certain implementations, the circuit includes at least one of an illuminating layer, a power storage layer and a sensor layer. The illuminating layer may include one or more microscale LEDs. In certain embodiments, the circuit is flexible. The circuit may be an electronic circuit including a circular printed circuit board having one or more electronic components and may measure from about 1 inch to about 3 inches in diameter. In certain exemplary embodiments, the diameter of the circuit is about 30 mm.

The apparatus may include an adhesive to attach the circuit to the gel. In certain embodiments, the circuit is disposed on the surface of the gel. The circuit may be integrally attached to the gel. In certain embodiments, the circuit is embedded in the gel. The circuit may be unitarily formed with the gel by dipping the circuit in a gel-based material prior to setting the gel. In other embodiments, a layer of gel-based material is disposed on the circuit, thereby embedding the circuit within the gel.

In certain embodiments, the apparatus includes a base mat or other backdrop structures adapted to receive one or more gels placed in electrical or optical communication with a base mat or other backdrop structures. The base mat may have one or more circuit elements adapted to receive one or more gels such that a circuit of the gel interacts with one or more circuit elements of the base mat. In certain embodiments, the base mat may include one or more interactive layers that include at least one of an illuminating layer, a touch sensitive layer and a display layer.

The base mat may be connected to a computer. The base mat and/or the gel may include magnetic elements. In certain embodiments, the base mat is substantially rigid including at least one of plexi, lexan, plastic, rubber, metal and wood. The base mat may include one or more layers of soft material including at least one of cloth, suede, felt, velvet, micro-fiber woven textiles, non-woven textiles and foam. The base mat and/or the gel may include a coating of at least one of allergen-proof material, mite-proof material, water-proof material and flame-resistant material. The base mat may be sized and shaped as desired and depending on the application without departing from the scope of the systems and methods described herein. In certain embodiments, the base mat is shaped as a square with sides having length from about 5 ft to about 10 ft.

In certain embodiments, the gel is formed with surface features adapted to supplement the sensory stimulation of the apparatus. In certain implementations, at least one surface of the gel includes a plurality of protrusions. The surface of the gel may have a variable thickness. The size, shape and/or the number of protrusions on the surface of the gel and/or the variable thickness may determine the texture of the surface. In certain embodiments, the texture of the surface substantially tactilely resembles a natural object such as rocks, flowers, trees, gravel or other objects.

The gel may be shaped as desired. In certain embodiments, the gel is shaped as at least one of a triangle, rhombus, hexagon, or any tessellable geometric shape. The gel may be sized as desired. In certain embodiments, the gel weighs from about 50 grams to about 200 grams and measures from about 1 inch to about 3 inches in thickness. The gels may be formed to interfit with other gels to form larger combinations. In certain embodiments, the apparatus includes a plurality of gels adapted to interfit with each other to form a unitary structure. The apparatus may include a plurality of gels adapted to be positioned in a predetermined arrangement.

In certain embodiments, the apparatus includes a case to package the gel. Exemplary cases may have flat panels that are configured to accept and removably attach to the gels. In such examples, the case may include soft-packaging material including at least one of felt, velvet, suede, woven textiles, non-woven textiles, recycled materials, paper and foam. A case may also be provided that is large enough to package the gel and the base mat.

In another aspect, the systems and methods described herein include methods of manufacturing a sensory stimulation apparatus for childhood cognitive development. The methods include providing a mold having an opening on a surface, such that a perimeter region of the opening extends above the surface of the mold, pouring gel-based material into the mold up to about the level of the surface, and positioning a circuit on the gel-based material through the opening such that at least a portion of the circuit fits within the perimeter region of the opening and above the surface of the gel. In certain embodiments, the opening may be configured to receive a printed circuit board. The methods may also include pouring gel-based material over the circuit thereby embedding the circuit. In certain embodiments, the gel-based material includes at least one smart substance that provides the optical property for the gel. In certain embodiments, smart substances comprise about 0.001% to about 0.1% of the gel.

In another aspect, the systems and methods described herein include a sensory stimulation apparatus having an at least partially transparent, pliable gel having an optical property, and a circuit for delivering electromagnetic radiation to the gel to modify the optical property. In certain embodiments, the gel is shaped as at least one of a triangle, rhombus, hexagon and tessellable geometric shapes. The gel may weigh from about 50 grams to about 200 grams and may be about 1 inch to about 3 inches thick.

In certain embodiments, the circuit includes a circular printed circuit board having one or more electronic components. The circular printed circuit board may have a diameter of about 1 inch to about 3 inches.

In certain embodiments, the apparatus further comprises a base mat, adapted to receive one or more gels. In certain embodiments, the base mat includes at least one of plexi, lexan, plastic, rubber, metal and wood. In certain embodiments, the base mat includes one or more layers of soft material including at least one of cloth, suede, felt, velvet, micro-fiber, woven textiles, non-woven textiles and foam. In certain embodiments, the base mat is shaped as a square with sides having length of about 5 ft to about 10 ft. In one embodiment, the apparatus comprises a computer in communication with the base mat.

In certain embodiments, the apparatus further comprises a case to package the gel and the base mat. In one embodiment, the case includes soft-packaging material including at least one of felt, velvet, suede, woven textiles, non-woven textiles, recycled materials, paper and foam.

In certain embodiments, the gel has a textured surface that includes at least one surface having a plurality of protrusions. In one embodiment, the texture of the surface substantially tactilely resembles a natural object. In certain embodiments, the surface of the gel has a variable thickness.

In another aspect, the systems and methods described herein include methods of manufacturing a sensory stimulation apparatus. The methods include providing a mold having an opening on a surface, such that a perimeter region of the opening extends above the surface of the mold, pouring gel material into the mold up to about the level of the surface, and positioning a circuit on the gel material through the opening such that the circuit fits within the perimeter region of the opening. In certain embodiments, the method further comprises mixing a photochromic compound with the gel material. In certain embodiments, method comprises mixing a smart substance with the gel material. The smart substance may include at least one of a photochromic compound, a halochromic compound, a thermochromic compound and an electrochromic compound.

BRIEF DESCRIPTION OF THE DRAWINGS

The following figures depict certain illustrative embodiments of the invention in which like reference numerals refer to like elements. These depicted embodiments may not be drawn to scale and are to be understood as illustrative of the invention and not as limiting in any way.

FIG. 1A depicts an exemplary sensory stimulation apparatus.

FIGS. 2A-2B depict the exemplary sensory stimulation apparatus of FIG. 1 assembled to provide sensory stimulation.

FIGS. 4A and 4B depict an exemplary base mat capable of interacting with the sensory stimulation apparatuses of FIGS. 1-3.

These and other aspects and embodiments of the systems and methods of the invention will be described more fully by referring to the figures provided and the following detailed description.

DETAILED DESCRIPTION

The systems and methods described herein will now be described with reference to certain illustrative embodiments, it being understood that the illustrated embodiments are not to be understood as limiting in any way.

As will be seen from the following description, the invention provides cognitive stimulation systems and methods of manufacturing the same. More particularly, in certain exemplary implementations the invention provides an at least partially transparent, pliable injection moldable material having an optical property, such as brightness or color, and a circuit for delivering electromagnetic radiation to the gel to modify the optical property. Under certain conditions, modifying the optical property can stimulate a user's visual and other senses to help improve cognitive development and functionality.

The illustrative apparatuses, systems and methods are described below in the following order: First, an illustrative sensory stimulation apparatus 10 having a pliable, injection moldable module is described. Second, the illustrative apparatus 10 is described in combination with one or more interactive layers that are configured for interoperation with the pliable module to provide supplementary stimulation to the user. Third, the illustrative apparatus is described in combination with a backdrop structure, such as a rigid base mat, to provide further interactive functionality for the user. Fourth, exemplary injection moldable materials and exemplary surface features, shapes and structures thereof are described in further detail. Fifth, exemplary systems are described that combine a plurality of the illustrative sensory stimulation apparatuses to provide modular development toys, puzzles, illuminated interactive games, and other sensory stimulation tools. Sixth, systems and processes for packaging the apparatuses and systems, and exemplary kits are described. Seventh, exemplary systems and methods for manufacturing molds and apparatuses are presented.

Figure 1B:
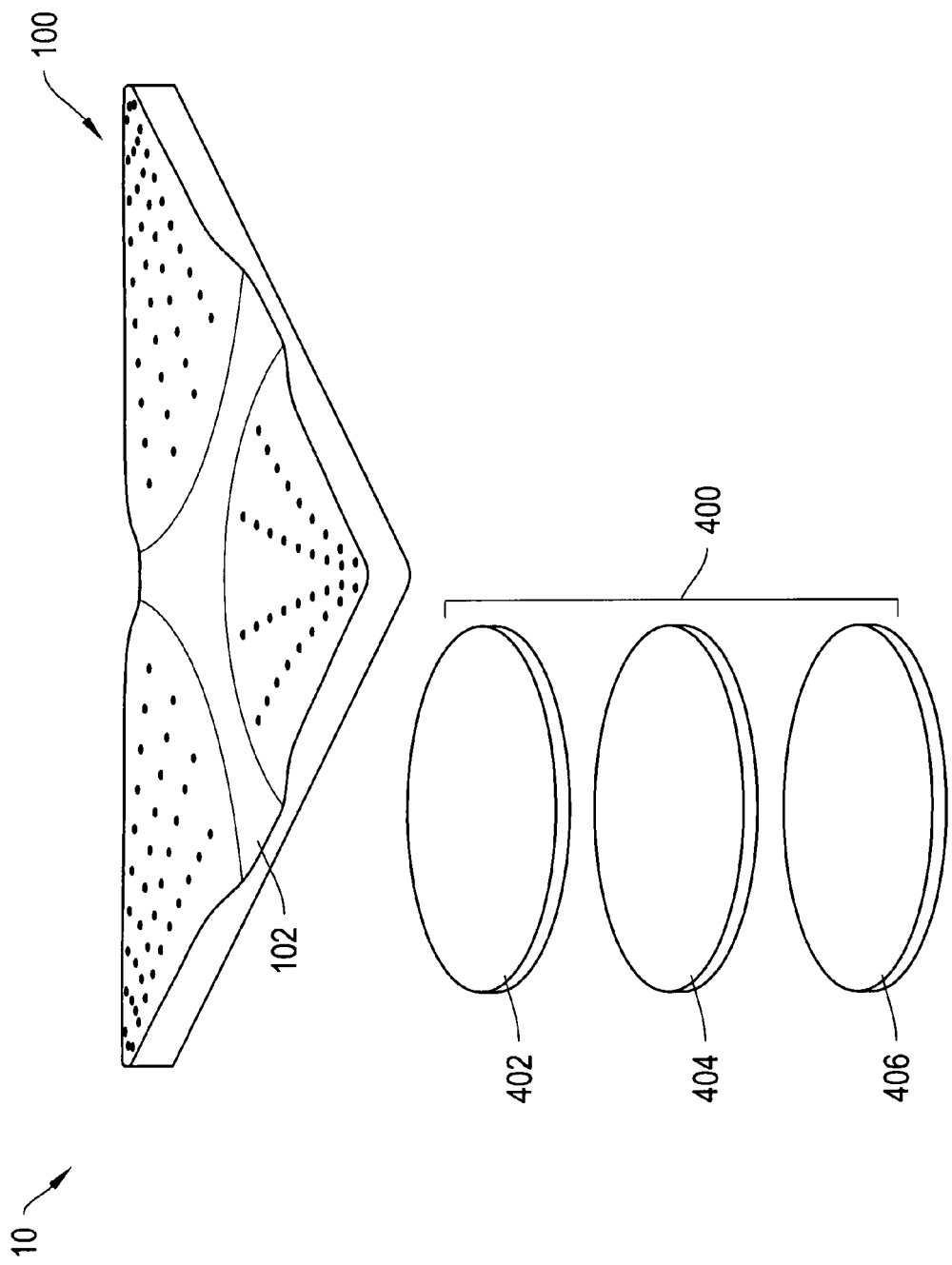
FIG. 1B depicts an exploded view of an exemplary sensory stimulation apparatus.

Turning to the illustrative embodiment, FIGS. 1A and 1B depict an exemplary sensory stimulation apparatus 10 that includes a pliable module 100 and a circuit 400. The pliable module 100 has one or more optical properties, such as brightness and color. The circuit 400 is configured to provide electromagnetic radiation to the module 100 to cause one or more optical properties of the module 100 to change. For example, applying electromagnetic radiation to the module 100 could cause the module 100 to glow or change color.

The module 100 is made of a pliable, injection moldable material, such as gel or any suitable polymeric material, that is configured to receive and respond to the electromagnetic radiation. Exemplary gel materials include LEVAGEL™ or TECHNOGEL™ made by Technogel Italia Srl, Pozzoleone (VI) Italy. The material 102 may include polymer material, such as thermoset elastomers and other polymeric materials described in U.S. Pat. Nos. 5,362,834, 6,326,412 and 6,809, 143, the entire contents of which are herein incorporated by reference. In certain embodiments, the material 102 is optically conductive and/or dispersive. The material 102 may be soft to touch and elastic. In certain embodiments, the material 102 includes a shape-resilient material such as shape-resilient polymers. The material 102 may be transparent, translucent or opaque, as desired according to the application. The material 102 may have any desired color. In certain embodiments, injection moldable materials include other thermoplastic materials such as polystyrene, acrylonitrile, butadiene styrene, nylon, polypropylene, polyethylene, and polyvinyl chloride.

In certain embodiments, the material 102 is selected so as to allow the color, brightness or any other optical properties of the gel to change in response to external stimuli. In certain embodiments, the material 102 includes one or more substances capable of undergoing a chemical change in response to the application of certain stimuli, such as light, stress, temperature, moisture, acidity, electric fields and magnetic fields (such substances are referred to as "smart substances"). In operation, when electromagnetic radiation is applied to the gel 100 by the circuit 400, the smart substances in the material 102 undergo a chemical change that results in a change of color, increase in brightness, or change in any other optical property of the material 102. Exemplary smart substances are described in more detail below.

As explained above, the apparatus has a circuit 400 for providing electromagnetic radiation to the gel. As shown in FIG. 1B, which depicts an exploded view of the apparatus 10, the circuit 400 includes an illuminating layer 402 for generating light, a power storage layer 404 for powering the illuminating layer, and a charging layer 406 for charging and/or re-charging the power storage layer 404.

The illuminating layer 402 provides light from one or more light sources that may be used to stimulate the photochromic chemicals of the material 102 and thereby illuminate and/or stimulate the module 100. In certain implementations, the light source in the illuminating layer 402 includes one or more light emitting diodes (LEDs) having physical and energy transmission features as needed to elicit the desired change in optical properties of the apparatus. In certain embodiments, the illuminating layer 402 includes UV (ultraviolet) LEDs for generating electromagnetic radiation in the ultra-violet range of the spectrum. In other embodiments, the illuminating layer 402 includes white light or colored light LEDs for generating electromagnetic radiation in the visible range of the spectrum, and when applied to the material 102, causes the module 100 to glow. The illuminating layer 402 may also include organic LEDs. In certain embodiments, one or more microscale LEDs are used, being sized and shaped to be smaller than regular LEDs. In certain embodiments, the light source includes any commercially available LED such as those manufactured by Fairchild Semiconductor, South Portland, Me., USA. In certain embodiments the one or more LEDs are arranged in pre-defined patterns on the illuminating layer 402 such that the pattern resembles a desired shape. The one or more LEDs may be connected to other electronic components in manner similar to the circuit diagrams in the application notes of commercially available LEDs. In one exemplary implementation, the LEDs in the illuminating layer 402 are positioned to direct light at the module 100, whereupon the light interacts with the photochromic particles in the material 102 and causes the module 100 to absorb certain wavelengths of light; this typically results in a change in an optical property such as color or brightness of the module 100. In certain implementations, the illuminating layer 402 includes a plurality of LEDs capable of generating light at different wavelengths. During operation, different portions of the module 100 may appear to have different colors and different brightnesses depending on the nature of the LED in the circuit 400.

In certain implementations, the light source of illuminating layer 402 includes a combination of multiple colored radiation sources that provide a desired color or white light output distribution. For example, a plurality of colored lights such as LEDs of different colors (red, blue, green) or a single LED with multiple colored chips may be employed to create white light or any other colored light output distribution by varying the intensities of each individual colored light. In other embodiments, the light sources of illuminating layer 402 are infra-red light sources for generating electromagnetic radiation in the infra-red range of the spectrum. Other light sources may be provided that are capable of generating electromagnetic radiation in any other portion of the spectrum. Still other light source(s) may be provided, such as an arc lamp, an incandescent bulb which also may be colored, filtered or painted, a lens end bulb, a line light, a halogen lamp, a chip from an LED, a neon bulb, a fluorescent tube, a fiber optic light pipe transmitting from a remote source, a laser or laser diode, or any other suitable light source. The light source may also include piezo-actuated light sources capable of illuminating on application of a mechanical stress.

The illuminating layer 402 is powered by energy supplied by the power storage layer 404. The power storage layer 404 may include single-charge type energy sources or rechargeable energy sources. Single-charge energy sources are typically disposed after the energy stored within the single-charge energy source is drained. In certain embodiments, single-charge energy sources include disposable alkaline or mercury based batteries. In certain embodiments, the power storage layer 404 includes rechargeable energy sources. The rechargeable batteries may include one or more Lithium ion batteries. The rechargeable batteries may also include at least one of a lead acid, a nickel metal hydride and a nickel cadmium battery. In other embodiments, the rechargeable energy source includes other soft rechargeable batteries and/or solar cells. The rechargeable energy source may also include other capacitive storage type batteries.

The rechargeable energy sources of the power storage layer 404 may be charged or re-charged by the charging layer 406. The charging layer 406 is electrically connected to the power storage layer 404. In certain embodiments, the charging layer 406 is configured to charge the power storage layer 404 wirelessly. In such embodiments, charging layer 406 is configured to charge the power storage layer 404 by wireless planar inductive charging. In such embodiments, the apparatus 10 is placed on or near a charging surface of a base mat (described in more detail with reference to FIG. 5). The base mat contains electrically conductive wires or threaded coils that are wound around a magnetically permeable core (the "primary windings") and that extend substantially parallel to the charging surface. The charging layer 406 may also include a set of windings similar in structure to the primary winding in the base mat (the "secondary windings"). During charging, electric current is supplied to the primary windings in the base mat thereby energizing the coil and generating a magnetic field that extends into the region surrounding the primary winding. When the secondary winding is placed near the primary winding, the magnetic field couples with the secondary winding and generates an electric current therein, thereby transferring the energy required to the power storage layer 404 in the circuit 400. In certain embodiments, the charging layer 406 includes a plurality of windings. The charging layer 406 may also include one or more components described in U.S. Pat. Nos. 7,164,255, 6,888,438 and 6,501,364, the entire contents of which are herein incorporated by reference. In alternative embodiments, the charging layer 404 includes at least one of an AC-DC power supply or a DC-DC power supply.

The circuit 400 may also include one or more proximity sensors, temperature sensors, infra-red sensors and pressure sensors including commercially available sensors such as those manufactured by Analog Devices, Inc., Norwood, Mass., USA and Texas Instruments, Inc., Dallas, Tex., USA. In certain embodiments, the circuit 400 may include RFID (radio frequency identification) tags. The RFID tags may be passive tags having no internal power supply unit or active tags having a built-in power supply. In such embodiments, electrical current is induced in the RFID tags in response to external radio frequency signals. The induced electrical current may be sufficient to power an internal circuit and transmit a signal from the tag. The RFID tag may be included in the circuit 400 for at least the purpose of identification using radio waves. The sensors and RFID tags may be microscale sensors and/or nanoscale sensors having dimensions substantially smaller than the module 100. The circuit 400 may include any electronic component as required for a desired application. In certain embodiments, the circuit 400 includes a microprocessor and/or a microcontroller for performing calculations and operating one or more electronic components.

In certain embodiments, the circuit 400 includes filters such as optical filters that are disposed on the illuminating layer 402. The optical filter may include at least one of an absorptive filter, a reflective filter, a monochromatic filter, an infra-red filter, a polarization filter, an ultraviolet filter, a neutral density filter, an interferential filter, a longpass filter, a shortpass filter and a bandpass filter.

The charging layer 406, power storage layer 404 and the illuminating layer 402 of circuit 400 may be arranged in a single layer to form a single layer printed circuit board. In certain embodiments, at least one of the charging layer 406, power storage layer 404 and the illuminating layer 402 are arranged as physically separate printed circuit boards that may be stacked on top of each other. The layers 402, 404 and 406 may be attached to each other. The charging layer 406, power storage layer 404 and the illuminating layer 402 may be arranged in circuit 400 in any manner without departing from the scope of the invention.

In certain embodiments, the circuit 400 includes electronic components interconnected by conducting wiring. The electronic components may be disposed on insulating materials. The insulating materials may include interwoven sheets of glass fibers reinforced with epoxy resin. In certain embodiments, the insulating materials include at least one of FR-4, FR-2, Polyimide, getek, BT-Epoxy, Cyanate Ester, and Polytetrafluoroethylene (PTFE). In certain embodiments, the circuit 400 is flexible and the insulating material includes flexible substrates such as PYRALUX® manufactured by DuPont. In certain embodiments, the circuit 400 includes low cost materials such as phenolic resin-infused paper printed circuit board material. In certain embodiments, one or more electronic components in circuit 400 are adapted for flexible circuits. As an example, the power storage layer 404 may include flexible solar cells. The electronic components may be interconnected by flexible conducting wiring that may include electrified or conductive thread or yarn and conductive woven textiles.

In certain embodiments, the sensory stimulation apparatus 10 typically weighs between about 50 grams and about 200 grams so that it can be handled and operated by children. In other embodiments, the sensory stimulation apparatus 10 can weigh less than about 50 grams and greater than about 200 grams depending on the desired application. The sensory stimulation apparatus 10 may also be sized and shaped depending on a desired application. In certain embodiments, the module may range in thickness from about 1 inch to about 3 inches so that it can be handled and operated by children.

FIGS. 2A-2B depict top and bottom views of the exemplary sensory stimulation apparatus 100 in an assembled state. As shown, the circuit 400 is disposed on the bottom surface of the gel. In certain embodiments, the circuit 400 and/or the module 100 are attached by adhesive materials. In certain embodiments, the circuit 400 is embedded within the module 100. The circuit 400 may be coupled to the module 100 in any number of ways. As shown, the circuit 400 is spaced away from the center region of the triangle such that a portion of the circuit 400 extends outwardly from the edges of the module 100. The circuit 400 may be positioned at any location with respect to the module 100 so long as it can impart electromagnetic radiation to the module 100.

In another aspect, the apparatus 10 shown and described above may be combined with one or more interactive layers that are configured for interoperation with the pliable module 100 to provide supplementary stimulation to the user.

Figure 3:
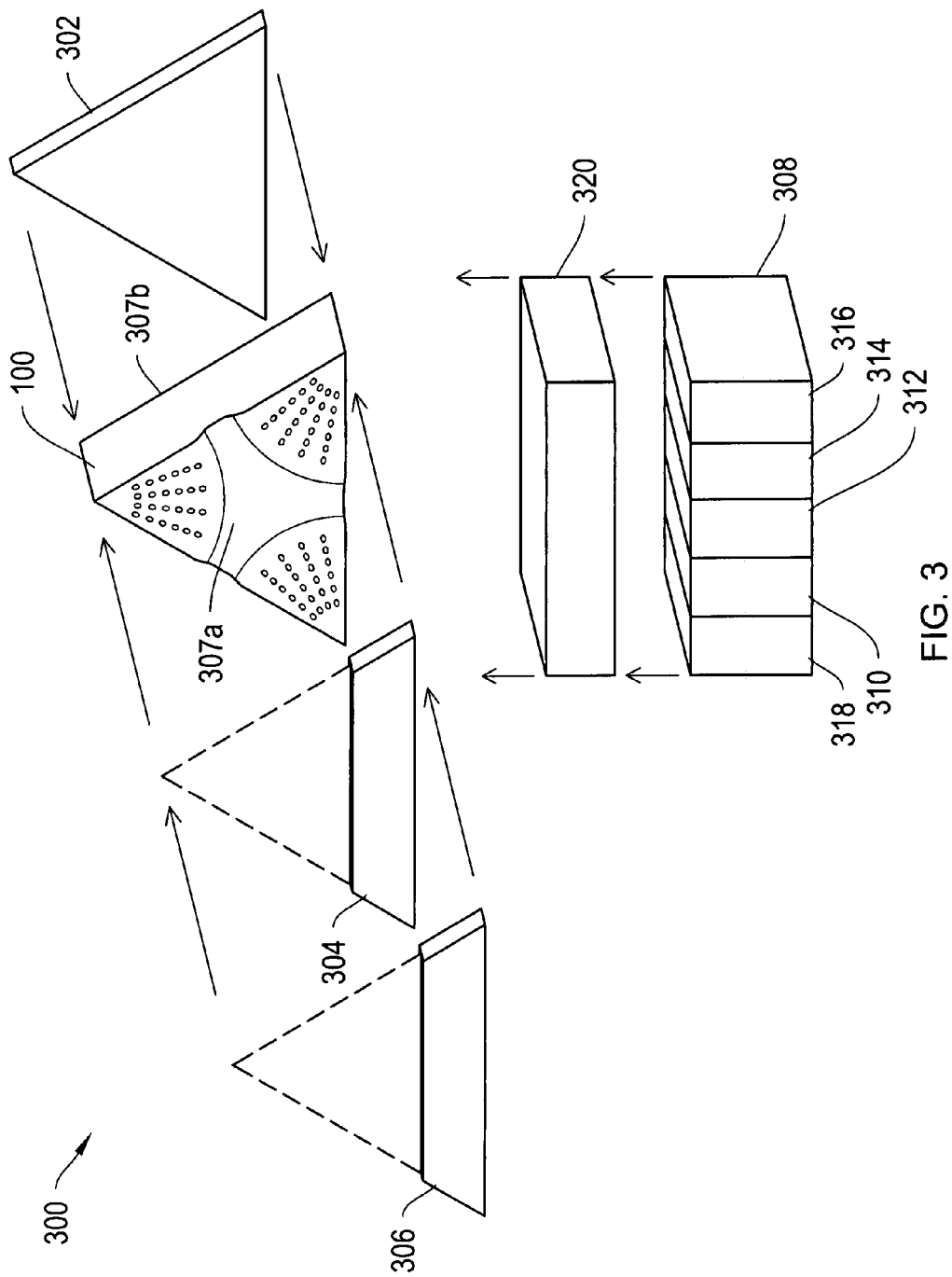
FIG. 3 depicts an exemplary sensory stimulation apparatus.

FIG. 3 depicts an exemplary implementation of the module 100 integrated into an interactive system that may stimulate one or more senses and aid in general cognitive function. In particular, FIG. 3 shows an exploded view of an interactive three-dimensional textured shape assembly 300 having a gel module 100 and one or more interactive layers to provide stimulation to the user. The illustrated interactive layers include a backlight layer 302 disposed adjacent to surface 307b of the gel 100 for illuminating the gel 100, a display layer 304 for displaying text and graphics, and a touch-sensitive layer 306 disposed adjacent to surface 307a of the gel 100 for recognizing a user's touch and thereby providing tactile interactivity. The interactive layers of assembly 300 also includes a processing module 308 which measures and controls the operation of the backlight layer 302, display layer 304 and touch-sensitive layer 306. The interactive layers 302, 304 and 306 are connected to the processing module 308 through an interface module 320. The interface module 320 provides an electrical and physical link between the processing module 308 and one or more of the backlight layer 302, display layer 304 and touch-sensitive layer 306.

In operation, the assembly 300 is configured to simultaneously stimulate the user's tactile senses through the touch and feel of the pliable gel module 100 and the user's visual and auditory senses through sound, light, text, imagery or other products arising from the electrical activation of the assembly 300. In one implementation, when a user touches the touch sensitive layer 306, the backlight layer 302 is activated to illuminate the gel 100, and the display layer 304 is activated to display text or a graphical image. More particularly, when the user touches the touch sensitive layer 306, the circuitry in the touch sensitive layer 306 sends an electrical signal to the processing module 308 through the wires and connectors in the interface module 320. The microprocessor subsystem 312 in the processing module 308 processes the electrical signal from the touch sensitive layer 306 and sends a control signal to the backlight layer 302 and the display layer 304. In response to the control signal from the microprocessor subsystem 312, the backlight layer 302 sends a control signal to a light source, which activates the light source and illuminates the gel 100, and to the display layer 304 to activate circuitry to display a body of text or a graphical image.

The backlight at layer 302, display layer 304, and touch sensitive layer 306 of the exemplary assembly 300 and their interoperation will now be described in further detail. The backlight layer 302 of the assembly 300 may include a light source to illuminate the gel 100. The light source in the backlight layer 302 is similar to the light source in the illuminating layer 402 described above and may include one or more light emitting diodes (LEDs) having physical and energy transmission features as needed to elicit the desired change in optical properties of the assembly 300. In certain embodiments, the light source in the backlight layer 302 includes an array of light emitting diodes (LEDs), as described above with reference to FIG. 1B.

The backlight layer 302 may also include other light source(s) such as an arc lamp, an incandescent bulb which also may be colored, filtered or painted, a lens end bulb, a line light, a halogen lamp, a chip from an LED, a neon bulb, a fluorescent tube, a fiber optic light pipe transmitting from a remote source, a laser or laser diode, or any other suitable light source.

Additionally, the light sources may be a multiple colored LED, or a combination of multiple colored radiation sources in order to provide a desired colored or white light output distribution. For example, a plurality of colored lights such as LEDs of different colors (red, blue, green) or a single LED with multiple colored chips may be employed to create white light or any other colored light output distribution by varying the intensities of each individual colored light. The light source may also include piezo-actuated light sources capable of illuminating on application of a mechanical stress.

The backlight layer 302 is shaped, sized, structured and positioned as needed to interoperationally fit with the pliable gel module 100. As shown in FIG. 3, the backlight layer 302 is shaped as a triangle, similar to the gel 100, to align the backlight layer 302 with the gel 100. The backlight layer 302 may be formed of another shape depending on the requirement of a specific application. The backlight layer 302 may be sized to cover at least a portion of the surface 307b. In certain embodiments, the backlight layer 302 may cover a section of the surface 307b having an area smaller than the area of surface 307b. The backlight layer 302 may be coupled to a portion of the gel module 100 for delivering light substantially directly into module 100. In certain embodiments, the backlight layer 302 is attached substantially flush with the surface 307b of the gel module 100. The backlight layer 302 may be attached to the surface 307b of gel 100 using a suitable adhesive. In other embodiments, the backlight layer 302 and the gel 100 is attached along the edges using suitable connectors (not shown).

The display layer 304 of assembly 300 is for displaying text and graphics to a user. The display may be configured to show text or images when activated electrically or by user stimulus such as touch. For example, the display layer 304 may be an electronic display, such as a flat panel screen. In one implementation, the display layer 304 includes an array of clear microcapsules with colored charged particles placed within that move in the presence of an electric field. When an electric field is applied across the material, the charged particles are realigned such that a one or more desired colored charged particles is visible from the surface of the display layer 304. By applying a desired electric field and establishing a desired pattern of realignment of the charged particles, the display layer 304 may appear to show a desired text or image.

The display layer 304 is controlled using suitable electronics internally within the processing module 308, or externally through an external computer system and may be updatable through programming. As an example, the electric field for the display layer 304 may be supplied in a controllable manner from the processing module 308 through the interface module 320.

In other embodiments, the display layer 304 includes a spatial light modulator such as those used in a liquid crystal display (LCD) or a field sequential color (FSC) display. The display layer 304 may also include a light source placed as a layer between the display layer 304 and the surface 307a of the gel module 100.

The display layer 304 may be shaped, sized, structured and positioned as needed to interoperationally fit with the pliable gel module 100. As shown in FIG. 3, the display layer 304 is shaped as a trapezium, to align the display layer 302 with the lower portion of the gel 100. The solid lines in the display layer 304 indicate the boundary of the display layer 304 and the dashed lines indicate the boundary of the underlying gel module 100. The display layer 304 may be formed of other shapes depending on the requirement of a specific application. The display layer 304 may be sized to cover at least a portion of the surface 307a. In certain embodiments, the display layer 304 may cover a section of the surface 307a having an area smaller than the area of surface 307a. In certain embodiments, the display layer 304 is attached substantially flush with the surface 307a of the gel module 100. The display layer 304 may be attached to the surface 307a of gel 100 using a suitable adhesive. In other embodiments, the display layer 304 and the gel 100 is attached along the edges using suitable connectors (not shown).

The touch-sensitive layer 306 of the assembly 300 is disposed on or near the display layer 304 for recognizing a user's touch and thereby enabling tactile interactivity. The touch-sensitive layer 306 typically includes a sensor that includes a layer of stored electrical charge and electrical circuitry for measuring an electrical property such as capacitance of the charge. This stored charge constitutes a capacitance which is a measure of the stored charge on the touch-sensitive layer 306 when a voltage is applied across it. When a user touches the touch-sensitive layer 306 with his or her finger, some of the charge is transferred to the user, consequently decreasing the capacitance of the charge on touch-sensitive layer 306. The reduction in capacitance is measured by the electrical circuits located at the corners of the touch sensitive layer 306 and in the processing module 308 which then calculates and identifies where the touch event occurred on the layer 306. Upon identifying the touch location, the processor 308 activates a lighting, sound, heating or other response, as described above. In one implementation, the top surface of the touch-sensitive layer 306 is coated with indium tin oxide or other suitable material that conducts a continuous electrical current across the surface.

In other embodiments, the touch sensitive layer 306 includes an electrically conductive and resistive metallic layer and electrical circuits to measure changes in the electric field. In such embodiments, an electric current (or an optical or other signal) is passed through the conductive and resistive metallic layers (which may optionally be held apart by spacers). The electrical current (or optical or other signal) generates an electric field within the layers. When a user touches the touch-sensitive layer 306, the conductive and resistive layers make contact in the location being touched, causing the electric field to change. The change in the electric field is measured by the electrical circuits and the coordinates of the point of contact are calculated in the processing module 308, as described above. The change in the electrical field can cause a signal to be sent to the processing module 308, as described above.

The touch sensitive layer 306 may be shaped, sized, structured and positioned as needed to interoperationally fit with the pliable gel module 100 and the display layer 304. As shown in FIG. 3, the touch sensitive layer 306 is shaped as a trapezium, to align the touch sensitive layer 306 with the lower portion of the gel 100. The solid lines in the touch sensitive layer 306 indicate the boundary of the touch sensitive layer 306 and the dashed lines indicate the boundary of the underlying gel module 100. The touch sensitive layer 306 may be formed of another shape depending on the requirement of a specific application. The touch sensitive layer 306 may be formed of another shape depending on the requirement of a specific application. The touch sensitive layer 306 may be sized to cover at least a portion of the surface 307a. In certain embodiments, the touch sensitive layer 306 may cover a section of the surface 307a having an area smaller than the area of surface 307a. In other embodiments, the touch-sensitive layer 306 is configured to not overlap with the display layer 304. In such embodiments, the touch-sensitive layer 306 and the display 304 are disposed on mutually exclusive sections of the surface 307a of the gel module 100. In certain embodiments, the touch sensitive layer 306 is attached substantially flush with the surface 307a of the gel module 100. The touch sensitive layer 306 may be attached to the surface 307a of gel 100 using a suitable adhesive. In other embodiments, the touch sensitive layer 306 and the gel 100 is attached along the edges using suitable connectors (not shown).

As indicated above, the operation of the backlight layer 302, display layer 304 and touch-sensitive layer 306 is measured and controlled by a processing module 308. The processing module 308 includes a microprocessor subsystem 312 for performing calculations such as the amount of electric current required to drive the backlight 302, the location on the touch-sensitive layer 306 being touched by the user, and the arrangement of the contents to be displayed on the display layer 304 in response to the user's touch. The microprocessor subsystem 312 also manages the operation of the other subsystems in the processing module 308. The microprocessor subsystem 312 includes a microprocessor chip or a microcontroller. The microprocessor chip may be preprogrammed to perform a particular function, such as sending a signal to the processing module 320 with instructions to cause back light layer 302 to illuminate, display text, or otherwise respond. The processing module 308 also includes a memory subsystem 316 that operates in conjunction with the microprocessor subsystem 312 to store measurements and calculations, coordinates on the assembly 300 where the apparatus 10 is located, and other features that are identified or performed by the microprocessor subsystem 312.

The processing module 308 also includes a communication subsystem 310 to link the assembly 300 with external components. In one implementation, the communication subsystem 310 links the assembly 300 with a computer placed remotely from the assembly 300. The communication subsystem 310 includes a radio frequency (RF) wireless transmitter-receiver ("transceiver"). The RF transceiver permits the assembly 300 to communicate with other devices that are external and unwired to the assembly 300. In one embodiment, the communication subsystem 310 includes suitable ports to provide wired connections with external devices. The ports in such embodiments may include at least one of parallel ports, serial ports, universal serial bus (USB). The ports in the communication subsystem 310 may be of other types depending on the desired application. The communication subsystem 310 may also connect the assembly 300 to a network of computers such as the Internet.

The processing module 308 of assembly 300 may include an audio subsystem 318. The audio subsystem 318 relays sound signals or plays music when the user touches the layer 306, thereby stimulating the auditory senses. During operation, in response to a touch received through the touch-sensitive layer 306, assembly 300 may produce sound (musical sequence) through the audio subsystem 318. The audio subsystem 318 includes a speaker and related electrical speaker driving circuit connected to the speaker to relay the sound to the user. The audio subsystem 318 may also include a microphone or a suitable acoustic sensor to detect sound that is then processed by the module 308 to cause sound, lighting or other interactive features of the pliable gel module 100 to emanate. In one implementation, the audio subsystem 318 is connected to the microprocessor subsystem 312 such that the processed sound received by the microphone is sent digitally to the microprocessor subsystem 312 to control the operation of the interactive layers. For example, upon receiving a voice input from a child trying to say a word, the assembly 300 performs voice recognition and illuminates the display 304 with a particular symbol, light, pattern, etc.

A power supply subsystem 314 is used to supply power to the electrical circuits and the interactive layers as needed. In one embodiment, the power supply subsystem 314 comprises soft batteries or solar cells.

As noted above, the assembly 300 includes an interface module 320 that links the processing module 308 including the power supply subsystem 314 and other components with the backlight layer 302, display layer 304 and touch-sensitive layer 306 to deliver power, data and control signals to and from the interactive layers. In certain embodiments, the interface module 320 includes one or more electrical conductors such as wiring and connectors to functionally and structurally connect the processing module 308 with one or more interactive layers. In other embodiments, the interface module 320 includes circuitry and metallic conductors to perform measurement operations as well as operations such as applying electric fields. The interface module 320 may be shaped, sized, structured and positioned as needed to interoperationally fit with the pliable gel module 100 and one or more of the processing module 308 and interactive layers 302, 304 and 306. In certain embodiments, the interface module 320 is formed at a location along the perimeter of the assembly 300.

In certain implementations, the one or more interactive layers are removable from the assembly 300. The backlight layer 302 may be removably attached to the gel module 100 such that a portion of a surface of the gel module 100 is covered by the backlight layer 302. The display layer 304 may be removably attached to a surface of the gel module 100. The touch sensitive layer 306 may be removably attached to a surface of at least one of the gel module 100 and the display layer 304. The interactive layers 302, 304 and 306 may be attached along any suitable surface according to the application. In other embodiments, the interactive layers 302, 304 and 306 may be attached along the sides. The interactive layers 302, 304 and 306 may be removably attached using suitable adhesives. In other embodiments, the interactive layers 302, 304 and 306 may be removable attached using connectors such as clips, locks and adhesive tape.

The interface module 320 and the processing module 308 are combined with gel module 100 to provide electrical connectivity, physical and electrical safety as well as pleasant aesthetics. The interface module 320 and the processing module 308 may be removably attached to at least one of the gel module 100 and the interactive layers 302, 304 and 306. In certain embodiments, a substantially rigid frame structure may be used to attach the gel module 100 to the interactive layers 302, 304 and 306, the interface module 320 and the processing module 308. The interactive layers 302, 304 and 306, interface module 320 and the processing module 308 may include wires and circuitry that may be suitably concealed within the frame structure such that the assembly 300 is aesthetically pleasing. The frame structure may be formed from plastic, wood, metal or resilient polymeric material.

In other embodiments, the gel module 100, the layers 302, 304 and 306, and the modules 308 and 320 are provided in a kit. In operation, the assembly 300 is activated when the interactive layers 302, 304 and 306, the modules 308 and 320 and the gel module 100 combine. As explained above, the circuitry of the assembly 300 is configured so as to send an electrical, optical or other signal to the processing modules 308 and 320 to identify the placement of a module 100 on the assembly 300. Similarly, the assembly 300 is configured to send a signal to identify the release of the module 100 from the assembly 300. The assembly 300 can thereby detect the number of modules 100 placed on the interactive layer 306 and the release of the modules 100 from the interactive layer 306. In operation, this signaling capability can be used to provide an interactive game. As an example, if a child places a gel module 100 on the separate interactive portion 306, the circuitry of the assembly 300 is activated, as described above, sends an electrical or optical signal to the processing module 308 and 320, and the number "1" will appear either on the interactive portion 304 or on a separate display screen connected to the interactive portion 304. As the child places the second textured surface unit on the interactive layer, the number "2" appears and so forth to help in counting.

In one embodiment, the interactive layers are embedded within the gel module 100 to combine certain functional components of the interactive layers. In certain embodiments, the functionality of the backlight layer 302 and the touch sensitive layer 306 are combined in a single structure. For example, as noted earlier, the gel module 100 may include piezo-actuated LEDs that function as both the backlight layer 302 and the touch sensitive layer 306. In another exemplary embodiment, the gel module 100 includes one or more inductive coils embedded in the gel material 102 to form a mutual inductance based proximity sensor, such as an antenna. In certain embodiments, the sensor includes at least one coil embedded in one gel module and a second (or more) coil embedded in one or more additional modules. When current flows in one module, a magnetic field is generated, which is sensed by other coils in adjacent modules. When two or more gel modules 100 having inductive coils are near each other, the magnetic field generated at one inductive coil may generate an electrical current in another inductive coil, which in turn may be used to operate a light source. In such an example, the inductive coil functions as an antenna to enable communication between two or more gel modules 100. In other embodiments, the interactive layers may be configured in a different order depending on the requirements of a particular application. In certain embodiments, inductive coils include conductive wires wound to function as an inductor. As noted earlier with reference to FIG. 1B, the apparatus 10 may include inductive coils for the purpose of charging the power storage layer 404 in the circuit 400. Inductive coils in the apparatus 408 interact with a base mat to transfer energy from the base mat to the circuit 400.

In certain implementations, the apparatuses described above are provided with a back drop structure to provide further interactive functionality. FIGS. 4A and 4B depict an exemplary backdrop structure 502 capable of interacting with the sensory stimulation apparatus 10 and assembly 300 described herein. The exemplary backdrop structure 502 is a base mat housed in a rigid exterior front surface 504 and a rigid back panel 514. It includes a charging surface 508 to provide power, an illuminating surface 510 to provide electromagnetic radiation to the apparatus 10, and an insulating surface 512. During operation, one or more apparatuses 10 are placed on the rigid surface 504 of the base mat 502. A power switch 520 may be turned on to electrically charge the apparatus 10 and illuminate the gel module 100. Portions of the module 100, having suitable smart materials, may change color or brightness depending on the nature of the illuminating source. Portions of the base mat 502 may include components and materials described with reference to circuit 400 or gel module 100.

The rigid surface 504 may be formed from any suitable rigid and durable material such as polymers, resilient polymers, plastics, fiberglass or metal. The rigid surface 504 may optionally include one or more layers of soft material. In certain embodiments, the back panel 514 also includes one or more layers of soft material such as cloth, velvet, felt, rubber, foam, gel or plastics.

As shown, the base mat 502 has a charging configured to charge the power storage layer 404 of apparatus 10 as described previously with reference to FIG. 1B. The base mat 502 includes a charging layer 508 having windings 516. The charging layer 508 may be similar to the charging layer 406 of FIG. 1. During charging, electric current is supplied through the switch 520 to the windings 516 in the base mat thereby energizing the coil and generating a magnetic field that extends into the region surrounding the winding 516. When the apparatus 10 is placed near the base mat 502, the magnetic field couples with the winding in the apparatus 10 and generates an electric current therein, thereby transferring the energy required to power the storage layer 404 of apparatus 10.

As shown, the base mat 502 has an illuminating surface 510 configured to illuminate or direct electromagnetic radiation to the gel module 100 of apparatus 10. The illuminating layer 510 has light sources 518 and a diffuser layer 506 for diffusing light from the light sources 518. The illuminating layer 510 may be similar to illuminating layer 402 of FIG. 1. During operation, the light sources 518 in the illuminating layer 510 direct light into the module 100. Portions of the module 100, having suitable smart materials, may change color or brightness depending on the nature of the light sources and the smart materials.

The base mat 502 also includes an insulating layer 512 and a back panel 514. The insulating layer 512 may include any suitable electrically and/or thermally insulating layer for protecting the user as well as the charging layer 508 and illuminating layer 510. In certain embodiments, the back panel 514 includes one or more layers of soft material such as cloth, velvet, felt, rubber, foam, gel or plastics. The insulating layer 512 and/or the back panel 514 may include molded resinous liquid materials such as PU foam having one or more sealant layers. Each of the layers are stacked together as shown in FIG. 4A. The base mat 502 also includes a power switch 520. In certain embodiments, the base mat 502 includes one or more shielding layers such as a ferrite sheet to reduce electromagnetic and radio frequency interference.

In certain implementations, the base mat 502 is configured with a plurality of light sources having different optical characteristics and located at different portions of the base mat 502. The module 100 may be moved around on the surface of the base mat 502 to overlap with one or more light sources. In such embodiments, since the light sources have different optical characteristics, the photochromic materials in the module 100 may respond differently to different light sources. During operation, the module 100 may appear to change color as a user moves it around on the base mat 502. In certain implementations, a plurality of such apparatus 408 are placed on the base mat 502 to form various patterns and shapes as shown in FIGS. 7-10D.

In certain embodiments, the base mat 502 is connected to a computer system for controlling and monitoring the operation of the windings 516 and the light sources 518. In such embodiments, the computer may include programmable software to control the operation of one or more components in the base mat 502.

In certain embodiments, an exemplary computer system includes a central processing unit (CPU), a memory, and an interconnect bus. The CPU may include a single microprocessor or a plurality of microprocessors for configuring computer system as a multi-processor system. The memory includes a main memory and a read only memory. The computer also includes the mass storage device having, for example, various disk drives, tape drives, etc. The main memory also includes dynamic random access memory (DRAM) and high-speed cache memory. In operation, the main memory stores at least portions of instructions and data for execution by the CPU.

The mass storage may include one or more magnetic disk or tape drives or optical disk drives, for storing data and instructions for use by the CPU. The mass storage system may also include one or more drives for various portable media, such as a floppy disk, a compact disc read only memory (CD-ROM), or an integrated circuit non-volatile memory adapter (i.e. PC-MCIA adapter) to input and output data and code to and from the computer system. The computer system may run a variety of application programs and stores associated data in a database of mass storage system.

The computer system may also include one or more input/output interfaces for communications, for data communications via the network. The data interface may be a modem, an Ethernet card or any other suitable data communications device. To provide the functions of a computer the data interface may provide a relatively high-speed link to a network, such as an intranet, internet, or the Internet, either directly or through an another external interface. The communication link to the network may be, for example, optical, wired, or wireless (e.g., via satellite or cellular network). Alternatively, the computer system may include a mainframe or other type of host computer system capable of Web-based communications via the network.

The computer system also includes suitable input/output ports or use the interconnect bus for interconnection with a local display and keyboard or the like serving as a local user interface for programming and/or data retrieval purposes. Alternatively, server operations personnel may interact with the system for controlling and/or programming the system from remote terminal devices via the network.

In certain embodiments, the components contained in the computer system are those typically found in general purpose computer systems used as servers, workstations, personal computers, network terminals, and the like. In fact, these components are intended to represent a broad category of such computer components that are well known in the art.

The methods involved herein may be embodied in a computer program product or software that includes a computer usable and/or readable medium. For example, such a computer usable medium may consist of a read only memory device, such as a CD ROM disk or conventional ROM devices, or a random access memory, such as a hard drive device or a computer diskette, having a computer readable program code stored thereon.

The systems and methods described herein may also be realized as a software component operating on a conventional data processing system such as a UNIX workstation. In such an embodiment, the process may be implemented as a computer program written in any of several languages well-known to those of ordinary skill in the art, such as (but not limited to) C, C++, FORTRAN, Java or BASIC. The process may also be executed on commonly available clusters of processors, such as Western Scientific Linux clusters, which are able to allow parallel execution of all or some of the steps in the present process.

Figure 5A:
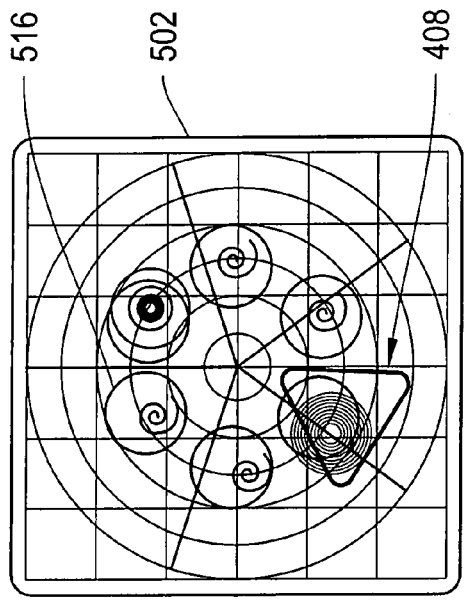
FIGS. 5A-5D depict the base mat of FIGS. 4A and 4B integrated with the sensory stimulation apparatuses of FIGS. 1-3 in various configurations.
Figure 5B:
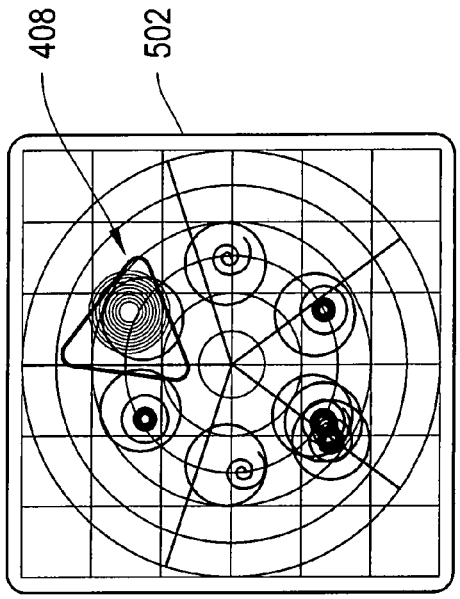
Figure 5C:
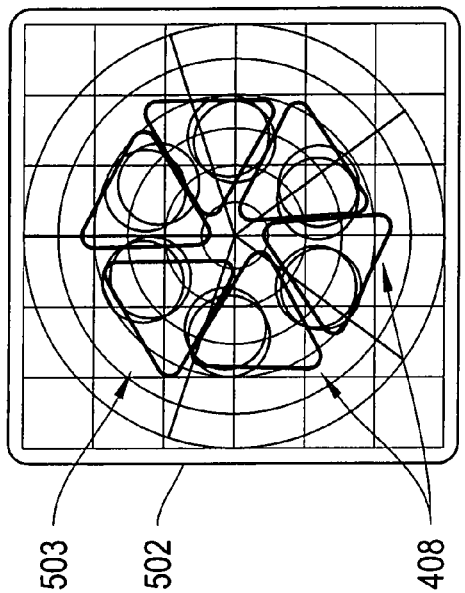
Figure 5D:
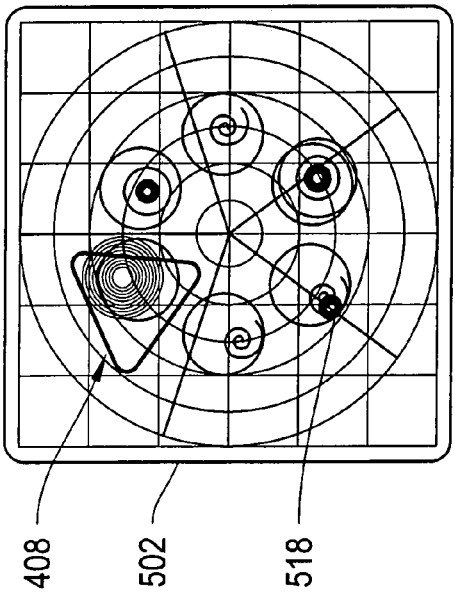

FIGS. 5A-5D depict the base mat of FIGS. 4A and 4B integrated with exemplary sensory stimulation apparatuses of FIGS. 1-3, an illustrative embodiment. Each of FIGS. 5A-5D depict the triangular shaped sensory apparatus 10 placed at different locations on the base mat 502. The light sources 518 in the base mat 502 may be illuminated in a pre-determined pattern, depending on the application. The illuminated light sources 518 are depicted as darker rings at the center of one or more windings 516. As shown in the first snapshot in FIG. 5A, a plurality of apparatuses 10 is placed next to each other to form a hexagonally shaped pattern 503. FIG. 5B depicts the triangular shaped apparatus 10 placed at the lower left hand portion of the base mat 502 and a light source 518 illuminated at the upper right hand portion. FIGS. 5C and 5D depict the triangular shaped apparatus 10 placed at the upper left hand portion and upper right hand portion, respectively, of the base mat 502 and three light source 518 illuminated on the base mat 502.

Having described exemplary sensory stimulation apparatuses and their integration into exemplary stimulation systems with interactive layers and backdrop structures, further discussion of exemplary injection moldable material will now be described, including optical property changing aspects of the material. As noted earlier with reference to FIG. 1A, the gel module 100 allows the color, brightness or any other optical properties of the gel to change in response to external stimuli. In certain embodiments, this is achieved through the use of smart substances mixed with or otherwise applied to the injection moldable materials (e.g., gel), as described above. The smart substances of material 102 may include at least one of photochromic, halochromic, electrochromic and thermochromic chemicals. Photochromic chemicals include substances or dyes that may reversibly or irreversibly change color upon exposure to certain electromagnetic radiation such as ultraviolet light. Photochromic chemicals that have a chemical structure that changes upon absorption of electromagnetic radiation. The change in chemical structure may cause the photochromic chemical to absorb a color (similar to a dye), and then change back to clear when the source of the electromagnetic radiation is removed. In certain embodiments, the photochromic chemicals change from one color to a different color by combination with a permanent pigment or dye. The photochromic chemicals may belong to a class of molecules including at least one of triarylmethanes, stilbenes, azastilbenes, nitrones, fulgides, spiropyrans, naphthopyrans and spiro-oxazines. In certain embodiments, the photochromic chemicals include REVERSACOL™ dyes manufactured by James Robinson, West Yorkshire, England. The material 102 may also include other photochromic substances described in U.S. Pat. Nos. 6,387,512, 6,303,673, 6,294,112 and 6,284,264, the entire contents of which are herein incorporated by reference. Halochromic substances change color when there is a change in acidity, thermochromic substances change color when there is a change in temperature and electrochromic substances change color in the presence of an electric field. In certain embodiments, the smart substances may also include at least one of luminescent, fluorescent or phosphorescent materials. These materials emit light of a selected wavelength when exposed to electromagnetic radiation of another wavelength. In such embodiments, the electromagnetic radiation from the light source in the backlight layer 302 causes the fluorescent or phosphorescent material of the gel module 100 to fluoresce or phosphoresce. In alternative embodiments (not illustrated), the gel module 100 may be wholly or partially illuminated by synthesizing light within the gel module 100. Electroluminescent or chemiluminescent materials and dyes may be included in material 102 of gel module 100 such that the gel module may be illuminated by the process module 308. Electroluminescence is the property of a material to emit light when an electric current is passed through it and chemiluminescence is the emission of light as a result of a chemical reaction. The material 102 may also include incandescent materials such that the shape or pattern illuminates when heated. The module 100 may be configured to illuminate and emit light in a broad band of wavelengths. The gel module 100 may also be illuminated to emit electromagnetic radiation in a narrow band of wavelength. In certain embodiments, the smart substances comprises from about 0.001% to about 0.1% of the gel module 100 on a weight per weight basis.

The material of the module 100 may also be selected to heat in response to a stimulus. In certain embodiments, heat is generated either within the gel module 100 or external to it upon activation of the processing module 708. Heating may be performed by a dielectric heating process whereby electromagnetic radiation heats the gel module 100. Heat may be applied to gel module 100 by subjecting the gel module 100 to an alternating electric field. In certain exemplary implementations a field is applied as the processing module 308 sends a signal through the interface module 320 to the gel module 100, which activates heating coils, causing heat to flow through the material 102. The applied heat may be used to change the geometry or reshape the surface of the gel module 100 to conform to a desired mold. In one embodiment, heat may be modulated in the gel module 100 using nanotechnology whereby nano-scale materials and devices are deployed in the gel module 100. More specifically, nano-scale embedded sensors may be utilized at selected locations with the module 100 to control the heating and cooling.

Figure 6A:
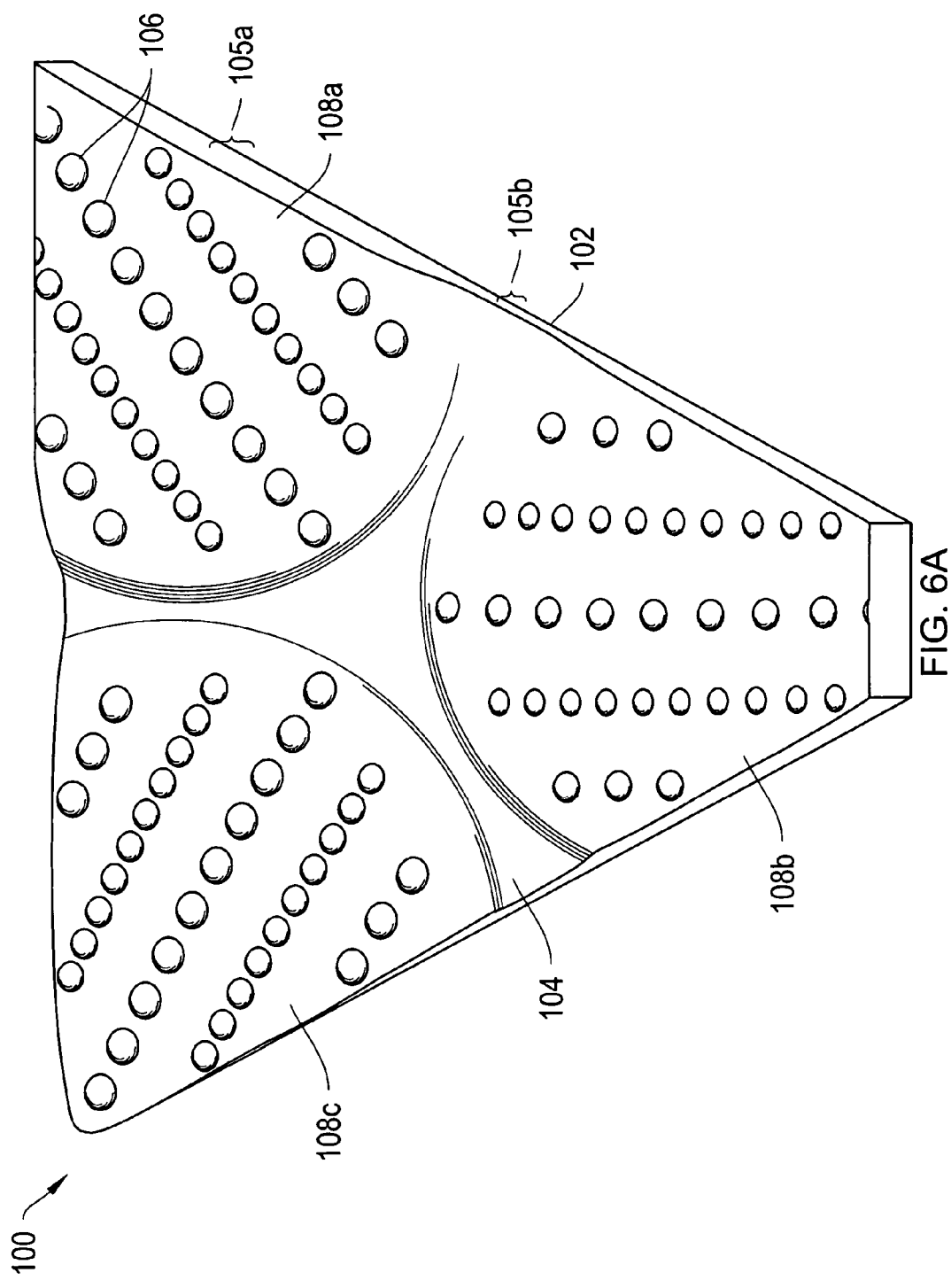
FIGS. 6A and 6B depict an exemplary gel material having a textured surface to provide sensory stimulation.
Figure 6B:
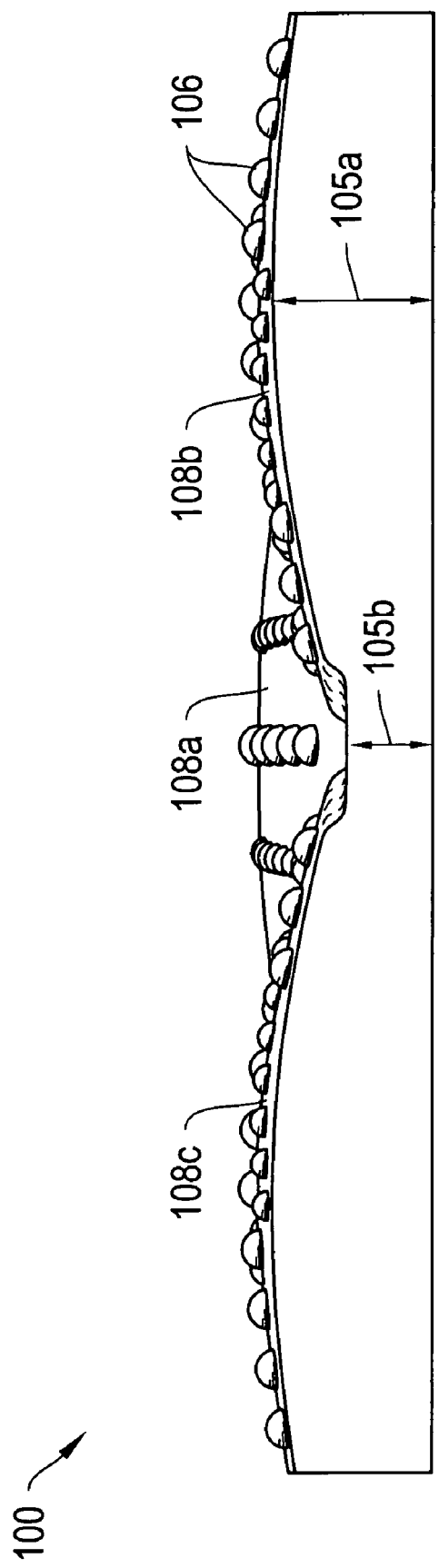

In another feature, noted earlier in FIG. 1A, the module 100 can be sized, shaped and structured to help supplement the cognitive development functionality of the apparatus 10. FIGS. 6A and 6B depict an exemplary material having a textured surface to supplement the sensory stimulation apparatus. More particularly, FIG. 6A shows a top view of a three-dimensional gel module 100 comprising a triangle shaped three-dimensional material 102. FIG. 6B shows a side view of the three-dimensional gel module 100. The gel module 100 has a variable surface 104 with a plurality of convex protrusions 106.

As more clearly seen in FIG. 6B, the gel module 100 has variable thickness including a plurality of relatively thick sections 108a-108c, with one or more of sections 108a-108c having thickness 105a at its thickest point. The material 102 also has a trough 104 extending around the interior perimeter of the thick sections 108a-108c and being comparatively thinner than the thick sections. These areas of increased 108 and decreased 104 thicknesses may be formed simultaneously with the gel module 100, or may be formed within an existing gel module 100 where the thick sections 108 are molded to a thin trough to form the thin sections 104.

The surface of gel module 100 may include one or more convex protrusions 106. In the illustrated embodiment, these protrusions 106 are higher than the surface 104 when placed on the surface 104 of the gel module 100. The protrusions 106 may be arranged in any suitable layout on the surface 104 of the gel module 100. The protrusions 106 may be formed of different heights and different base areas. The protrusions 106 may be formed of different geometries and shapes (e.g., spheres, blocks, half-moons, stars, thorns, flowers).

The texture of the surface of the gel module 100 may be defined by the protrusions 106 and the thickness variations. In particular, a texture is deemed smooth or coarse depending on the size, shape and layout of protrusions 106 as well as the surface undulations due to thickness variations. A user may stimulate their tactile senses by touching and running their hands over the uneven surface of the gel module 100 thereby sensing these surface undulations.

Figure 7:
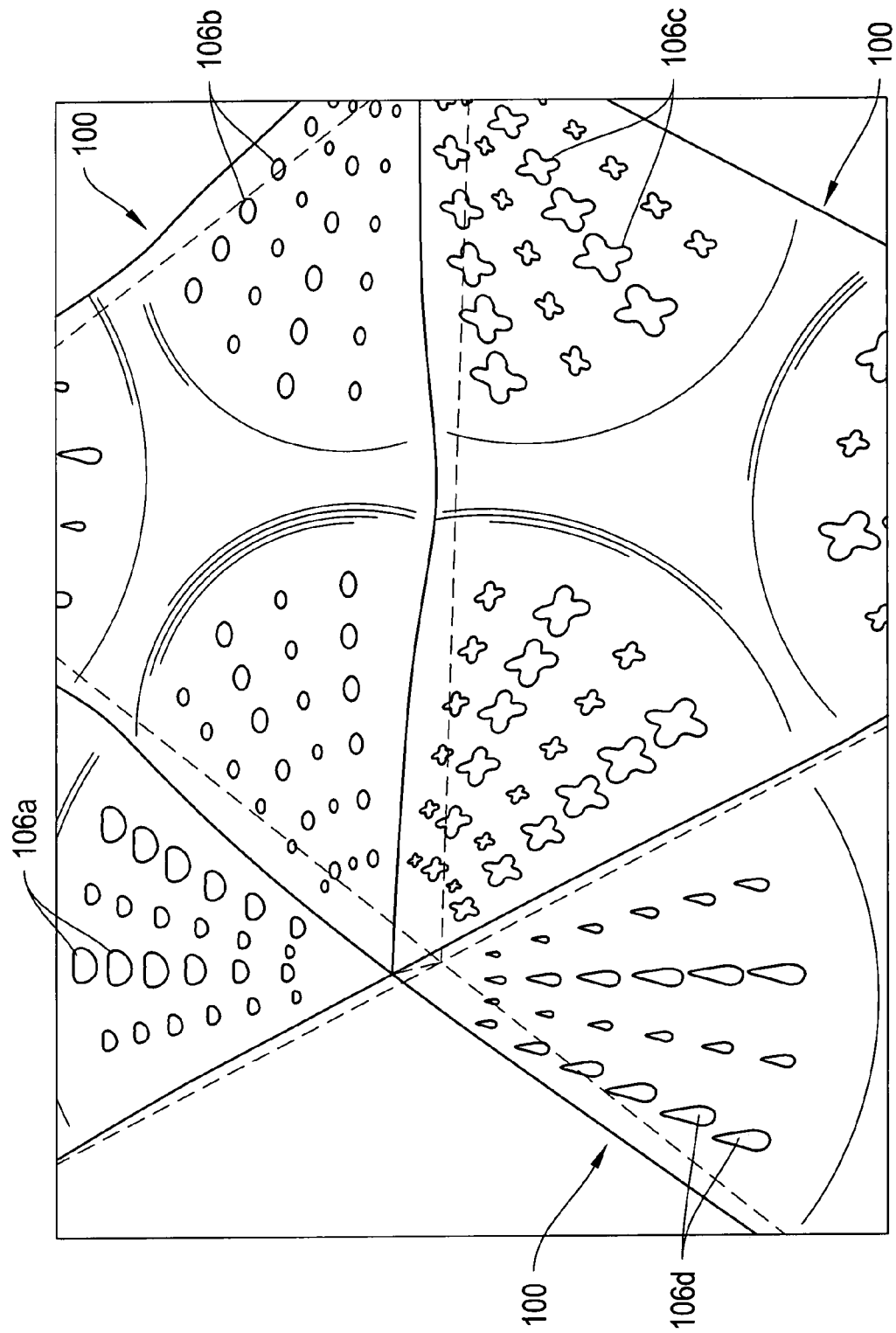
FIG. 7 depicts a plurality of textured sensory stimulation apparatuses having surface patterns.

FIG. 7 more particularly calls out exemplary protrusion geometries that may be adopted for the gel module 100. In one embodiment, the protrusions 106 may be formed to be symmetrically arranged on the surface of the gel module 100. The four gel modules 100 have protrusions 106a-106d, respectively, built on their surfaces 104 and 108. The protrusions 106 may include large hemispheric structures (splashes) 106a, small hemispheric structures (drops) 106b, floral structures 106c and sharp structures 106d.

Shown in FIG. 7 are a group of exemplary protrusions 106. To aid with tactile development and material recognition, these protrusions 106 may be configured in the form of natural textures. In the illustrated example, the protrusions 106a and 106b are shaped like water (liquid) splashes and droplets. The protrusions 106 may also be shaped as natural structures. In the illustrated example, the protrusion 106c is configured like one or more flowers. The protrusions 106 may also be configured with a combination of tactile and visual aspects of a structure. Protrusion 106d is made sharper like a thorn or a spike. The layout of these protrusions 106 may be modified to create different surface texture feels. Protrusions 106 may be configured to have different heights, base areas and shapes to create varying degrees of roughness and smoothness. Other protrusion 106 shapes include three-dimensional geometric shapes.

The gel module 100 has surface undulations and protrusions 106 and may be configured to have any suitable geometry. In one embodiment, the gel module 100 is formed in the shape of a triangle. The gel module 100 may also be combined with other modules to form a larger geodesic or hexagonal field pattern. In certain embodiments, the surface texture of the modules 100 of each of the apparatuses 10 in the larger pattern may be different from each other. In such embodiments, the texture of the combined hexagonally shaped pattern may be different at different locations. In other embodiments, the module 100 may be sized and shaped differently so as to combine with other modules 100 and generate one or more different patterns.

In one embodiment, the gel module 100 is configured with symmetrical sides and patterns. In another embodiment, the sides and patterns are asymmetrical. The gel module 100 may be formed with undulated or uneven sides to allow two of more of these shapes 100 to lock securely when combined. In certain embodiments, the edges and/or corners of the gel module 100 are sharp and/or rounded.

Having described exemplary sensory stimulation apparatuses, interactive layers, base structures, and features of the injection moldable materials, exemplary systems are described that combine a plurality of the illustrative sensory stimulation apparatuses to provide modular development toys, puzzles, illuminated interactive games, and other sensory stimulation tools.

FIG. 7 shows four triangular gel modules 100 placed next to each other. As shown, the gel modules 100 are placed next to each other to form larger geodesic field patterns. The gel module 100 may be combined with other gel modules 100 to form more complex shapes. The single triangular gel module 100 may be combined with rhombus and trapezoid gel modules 300 and 302 to form more complex hexagonal patterns.

Figure 8:
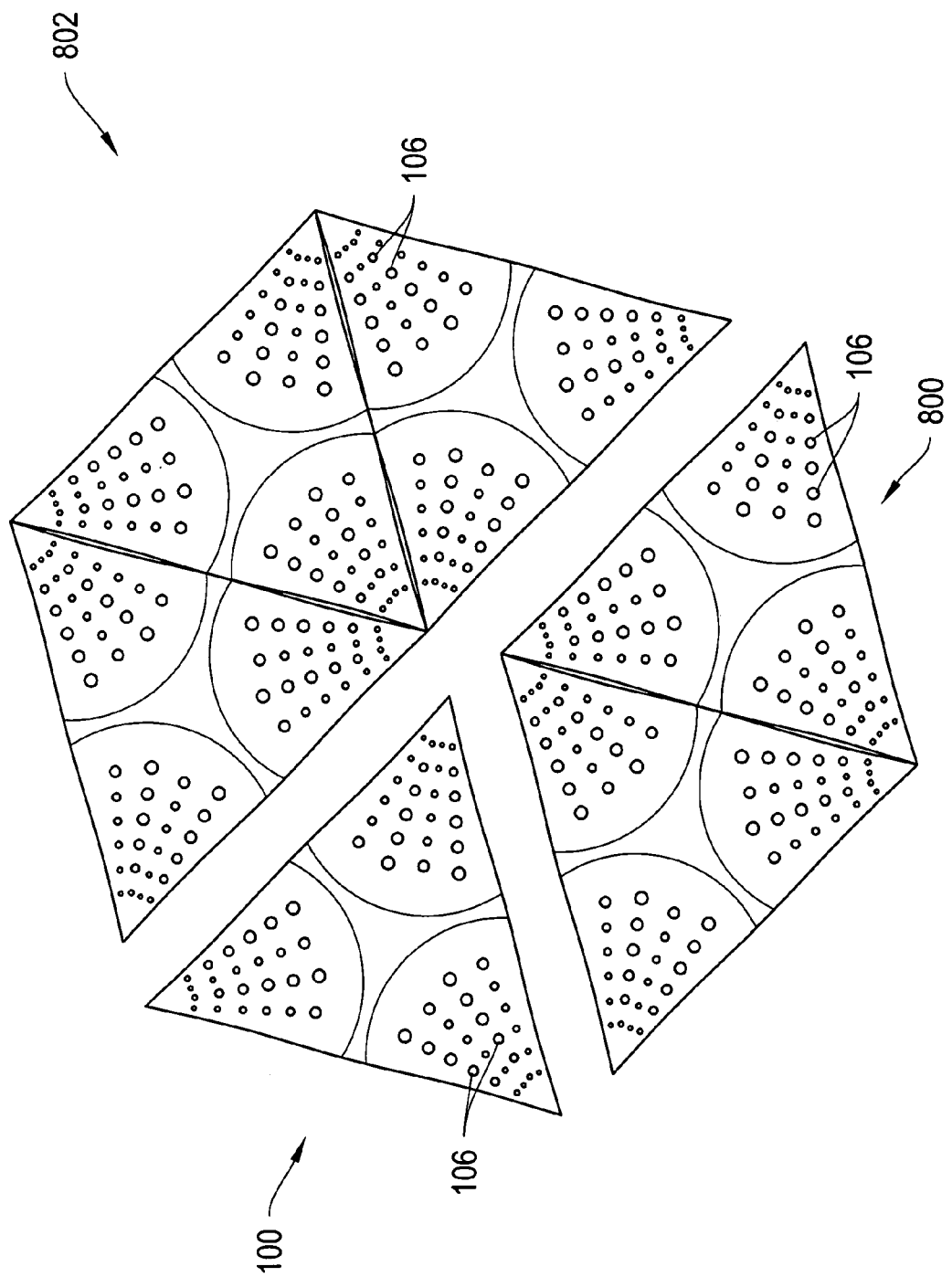
FIG. 8 depicts a plurality of textured sensory stimulation apparatuses arranged to form different shapes.

FIG. 8 depicts three-dimensional shaped, interactive modules of different shapes including a triangle 100, rhombus 800 and trapezoid 802. These shapes may be formed as one piece each or by combining a suitable number of triangle gel modules 100. The gel modules 100, 800 and 802 include protrusions 106. The gel modules 100, 800 and 802 may be combined with each other in any suitable combination without departing from the scope of the invention. The gel modules 100, 800 and 802 may include adhesives that permanently or removably attach the modules to each other. The gel modules 100, 800 and 802 may be combined with circuit 400 of FIG. 3 to form at least one sensory stimulation apparatus of different shapes.

Figure 9:
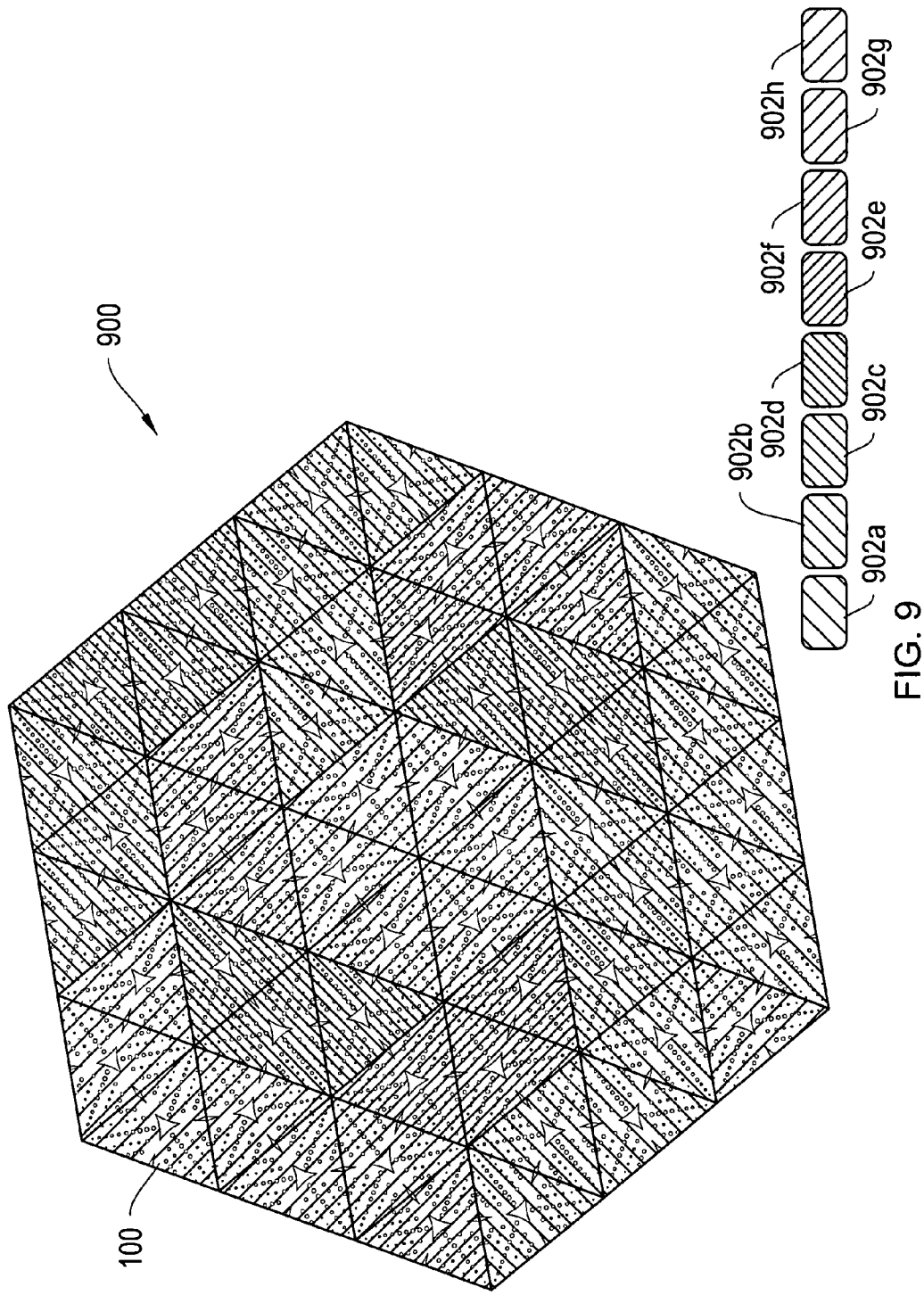
FIG. 9 is an assembled sensory stimulation system having a plurality of apparatuses of varying textures.
Figure 10:
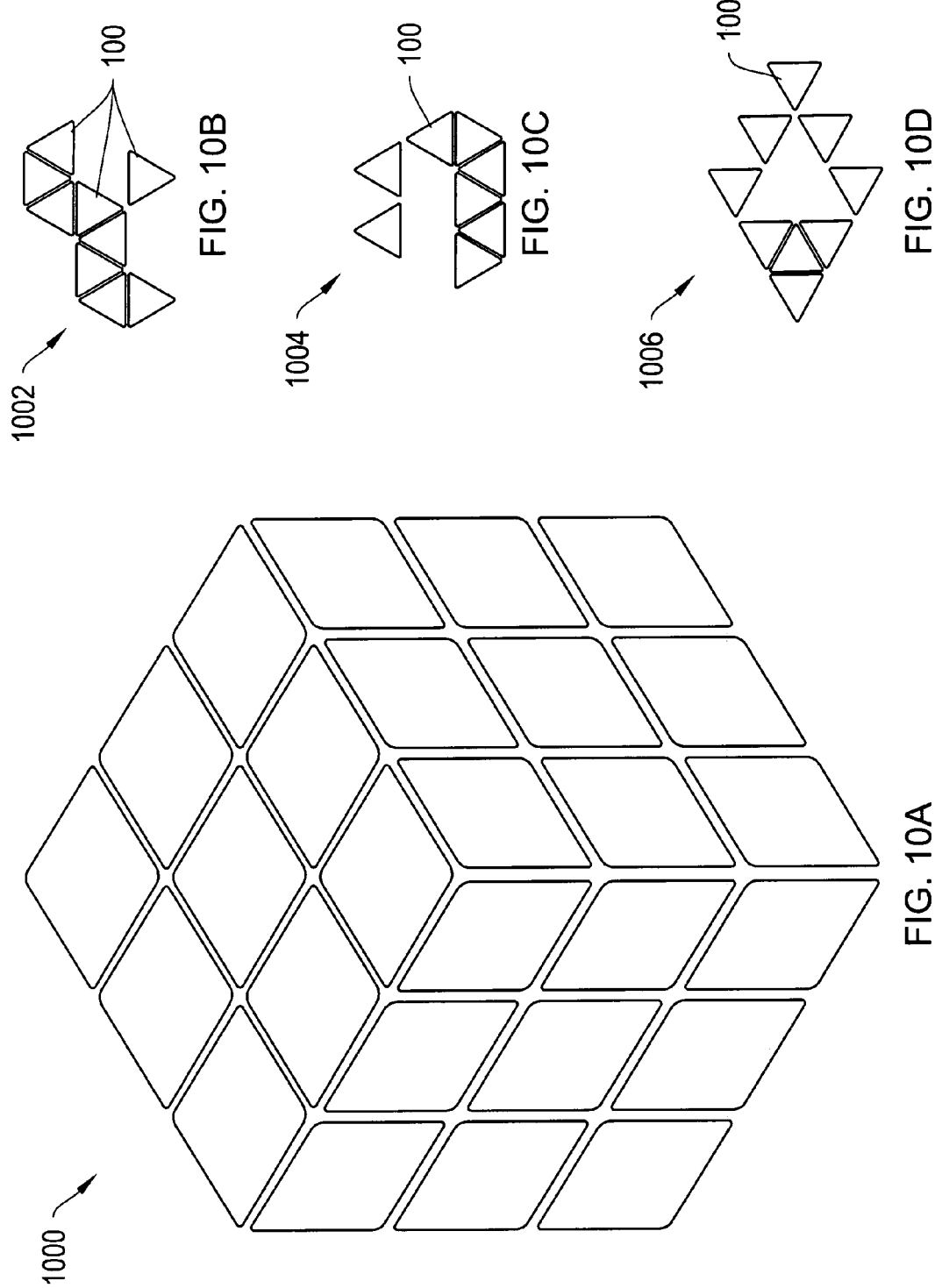
FIGS. 10A-10D depict another exemplary sensory stimulation system formed by combining a plurality of textured sensory stimulation apparatuses.

FIG. 9 shows an assembled three-dimensional shaped system structure 900 comprising three-dimensional gel modules 100, 800 and 802 of FIG. 8 combined in various arrangements. The three-dimensional shaped pattern 900 comprises a variation in texture as indicated by the shading legend 902a-902h (generally "shading 902"). At least one of apparatus 10, assembly 300 and modules 100 may be combined on the base mat 502 (shown in FIGS. 4A and 4B) to form systems 800, 802 and 900. In such embodiments, the base mat 502 may be interactive, such that the base mat 502 provides a visual or auditory signal (such as illuminating a light source) in response to the formation of a desired pattern such as 800, 802 and 900. In other embodiments, the base mat 502 is connected to computer configured with an image processing engine for identifying the pattern of the apparatus 10 placed on the base mat 502.

Structures of this type may be configured to form toys, puzzles, games and other tools. FIGS. 10A-10D depict exemplary systems formed by combining a plurality of modules, such as the modules of FIGS. 1-4C. FIG. 10A depicts a cube formed from rhombus gel modules. FIG. 10B depicts an animal 1002 formed from about eight triangle gel modules. FIG. 10C depicts a boat 1004 formed from triangle gel modules and FIG. 10D depicts a fish 1006 formed from triangle gel modules. In certain implementations, the modules of FIG. 1-4C are placed on the base mat 502 in a pattern similar to patterns 1000, 1002, 1004 and 1006. In such implementations, the base mat 502, optionally in combination with a computer, may be capable of recognizing the source of the attempted pattern and display to the user a guess. As an example, a user arranges nine apparatuses 408 in the shape of a fish 1006 as shown in FIG. 10D. Depending on the placement of each of the nine apparatuses 408, a computer connected to the base mat 502 identifies that the attempted pattern is that of a fish and provide a display to a user stating "It is a fish!"

In one aspect, the apparatuses, systems and methods of the invention include an ornamental design for a sensory stimulation apparatus. In certain embodiments the ornamental design is reflected in the FIGS. 1A-10D.

In one implementation, a collection of gel modules 100 or patterns 800, 802 and 900 is provided along with suitable layers that form part of an interactive system (for example, a game or puzzle such as chess with individual pieces arranged together to form a larger pattern) having a plurality of shaped assemblies 300 or apparatuses 10 that simultaneously stimulate sight, hearing and tactile senses, while improving problem solving and creative thinking capabilities. Such a system may include an electrically conductive woven Nylon hook and loop system such that the modules and patterns may be illuminated and desired information and images may be displayed.

In certain embodiments, the systems and methods described herein include games and/or educational tools in which the base mat 502, described earlier with reference to FIGS. 4A and 4B, is used in combination with apparatus 10, such that the apparatus 10 and the base mat 502 interact to stimulate a user's visual and other senses In an exemplary embodiment, the base mat 502 is configured in the form of a board game having individual square shaped regions that are representative of squares on a chess board. One or more of the square shaped regions may include electronic components such as light sources and charging wires, as described above, capable of illuminating the base mat 502 or charging the apparatus 10 of FIGS. 1A and 1B. Apparatus 10 may be sized and shaped as chess pieces such as a king or a queen. Individual chess pieces may have interactive features, whereby they are configured with suitable electronic components such as LEDs for illumination and charging wires to charge the apparatus 10. The base mat 502 board is configured with pre-programmed software that includes computer code programmed with a set of chess rules that identify allowed movements (e.g., a bishop is allowed to move diagonally), rules for capture and release of chess pieces (e.g., a knight that lands on a base mat 502 square occupied by an opposing player's piece is allowed to replace the opposing player's piece on the square), check, and check mate rules. The mat 502 also includes a sensor, similar to those described herein, that identify when a piece is placed on a particular square on the mat 502. During operation, when the interactive chess pieces are positioned and moved on the square shaped region on the base mat 502, the circuitry of the base mat 502 is activated, as described above, and portions of the base mat 502 and/or the chess pieces are illuminated to signal an appropriate move, disallowed move, capture, check, or check mate. In certain embodiments, the base mat 502 and the apparatuses 10 are configured to teach chess to a learner such that at least one of the base mat 502 and the apparatuses 10 illuminate in response to the learner's actions. As an example, a particular set of squares on the base mat 502 may be illuminated to teach the learner about possible chess moves for a particular chess piece. In other embodiments, one or more chess pieces may be illuminated to suggest a move to a learner. The apparatus 10 and base mat 502 may be combined and integrated in any suitable way depending on the desired application.

While the examples described above illustrate the use of the interactive materials as sensory stimulation and educational tools, such materials may be employed for other purposes. The gel module 100, apparatus 10 and the assembly 300 may be used as a medical device. In one particular application, the assembly 300 and surfaces created therein may be used for physiotherapy and massage treatments. A combination of varied textured surfaces and features such as heat synthesis may help relieve trauma and relax tight muscles. In another implementation, the module 100 according to the invention may be used as seat cushions in combination with heating elements. In such an application, temperature sensors and suitable electronics are included in one or more interactive layers within the module 100 to help maintain comfortable body temperatures.

In yet another implementation, the apparatus 10, assembly 300 and patterns 800, 802 and 900 form more complex assemblies, such as interactive wall hangings, floor coverings and carpeting with layers of infra-red motion sensors, temperature sensors, light emitting materials, sound generating devices and display devices, that allow indoor and outdoor environments to be interactively controlled through the processing module 308 to suit aesthetic needs. The assembly 300 or gel module 100, may also be used as a bumper zone in infant cribs. The assembly 300 or gel module 100 may be used in conjunction with floor coverings as a toddler signaling system to monitor the location and activity of toddlers as they move around.

In another implementation, the gel module 100 according to the invention may be combined with peripheral devices such as motors, actuators and vacuum pumps to move or modify the textured surfaces. In such an implementation, the gel module 100 may be combined with interactive layers having motors, actuators and vacuum pumps that are controlled and operated through a processing module 308 similar to the assembly 300. In one implementation, an additional interactive layer may be attached to the surface 307b of the gel module 100. This additional layer may include openings or apertures that connect to and operate a vacuum pump.

The gel modules 100, the assembly 300, the base mat 502 or the systems 800, 802 and 900 may be packaged in packaging to assist in transportation and storage. The cases may comprise flat panels of packaging material such as plastic, cardboard or aluminum. The flat panels may be configured to accept and removably attach to the gel modules 100, assembly 300 or patterns 800, 802 and 900. The gel modules 100, may attach to the case through suitable connectors. The flat panels may include removable connectors such as the 3M DUAL LOCK™ made by 3M Company, Maplewood, Minn. The connectors used for attaching the gel modules 100 to the case may include other types without departing from the scope of the invention. The case may further include handles attached to the flat panels at suitable locations. In one embodiment, the handles are straps attached to two locations on the flat panel.

In certain embodiments, the cases may be flexible and may be formed from soft-packaging material such as felt, velvet, suede, or other suitable material. In other embodiments, the soft-packaging materials such as felt, velvet and suede may be included as a layer in a portion of the case. The cases may be formed from bio-degradable material and portions of the case may be dissolvable in water. In certain embodiments, the case may contain waterproof material such as GORETEX™. The case may also include sealant materials to keep certain liquids such as water from damaging the gel modules 100. Different portions of the case may be formed from different materials. In other embodiments, the case may be formed unitarily from a single piece of material such that substantially all surfaces are smooth and continuous.

In some embodiments, the cases are collapsible and may contain suitable tabs, inserts and slits to enable reassembly. The cases may also include suitable connectors such as tape, VELCRO™, buttons, adhesive to assist in reassembly.

The cases may comprise openings and apertures to view and touch the gel modules 100, apparatus 10, assembly 300 or patterns 800, 802 and 900 placed within. In certain embodiments, the apertures and openings may be sealed with glass, translucent plastics or transparent plastics such that external environmental damage is minimized.

In one aspect, the case may include suitable ornamental designs that may include images of the gel modules 100, assembly 300 or patterns 800, 802 and 900, and instructional and material information. The case may include labels having these designs such that the labels may be either permanently or removably attached. The labels may be formed from suitable material including plastic, glass, paper, felt, velvet or suede. The labels may also be formed from a material similar to the material of gel module 100.

In one implementation, the gel module 100, assembly 300 or patterns 800, 802 and 900 may be packaged in a case and further combined with accessories to form a child-entertainment or child-educational kit. In one embodiment, the accessories include an instruction manual. In such an embodiment, the instruction manual may be formed from waterproof material. The instruction manual may be flexible and may be formed from plastics, paper laminated in plastics and flexible polymeric materials. The instruction manual may also be formed from rigid materials such as wood, rigid plastics and metal. The instruction manual may be used to provide suitable assembly instructions for the gel module 100 as well as the case.

In other embodiments, the accessories include a rope leash formed from suitable materials such as flexible polymers and synthetic and natural fibers. The leash may be attached on one end to a portion of the case and/or the gel module 100 such that the case and/or the gel module 100 may be easily pulled from one location to another using the unattached end. The leash may also be formed from rigid material such as plastics, metal or wood such that the case and/or the gel module may be pushed from one location to another by applying a force on the leash.

In still other embodiments, the accessories include wheels attached to the case and/or the gel module 100. The attached wheels help with moving the case and/or the gel module 100 from one location to another. One or more wheels may be attached to a portion of the base of the case such that the case and its contents may be moved on a horizontal surface. In certain embodiments, two or more wheels may be connected close to one another and positioned on an edge or side of the case. In such embodiments, the two or more wheel combination may assist in transporting the case up a flight of stairs.

Having described exemplary apparatuses having injection moldable materials configured with the circuitry to provide sensory stimulation, integrated into exemplary systems, and exemplary materials and applications and other features, exemplary methods of manufacturing such apparatuses and systems are now described. According to one embodiment, a user can use modeling software to create interactive modules 100 having textured surfaces. Such software is used to generate parameters for modeling basic 3D shapes and run a script (algorithm) using these basic shapes to generate a complex array of surfaces and shapes. Exemplary methods for generating module 100 and apparatuses 10 having modules 100 and circuits 400 are described in FIGS. 11-13. The software may also be used to generate parameters for modeling and shaping molds. The generated molds may be used to form the 3D shapes in a suitable injection molding process.

In one embodiment, the mold is formed from a rigid material including hardened steel and aluminum. In other embodiments, the molds may be formed from soft materials. The molds may be triangular in shape and have a cavity in their central portion. The mold may include a suitable receptacle to attach a circuit 400 to the gel module 100. The cavity includes topological features such as surface undulations and recesses. These topological features are transposed onto a gel type material during an injection molding process to form a gel module 100 having protrusions. The protrusions on the gel module 100 are formed from the gel type material filling the cavities and recesses in the mold and thereby acquiring the corresponding shapes. The molds may have any suitable geometry. The size and shape of the recesses and cavities shown in the figures illustrated herein may be selected based at least in part on the desired surface topology and protrusion geometry.

Figure 11:
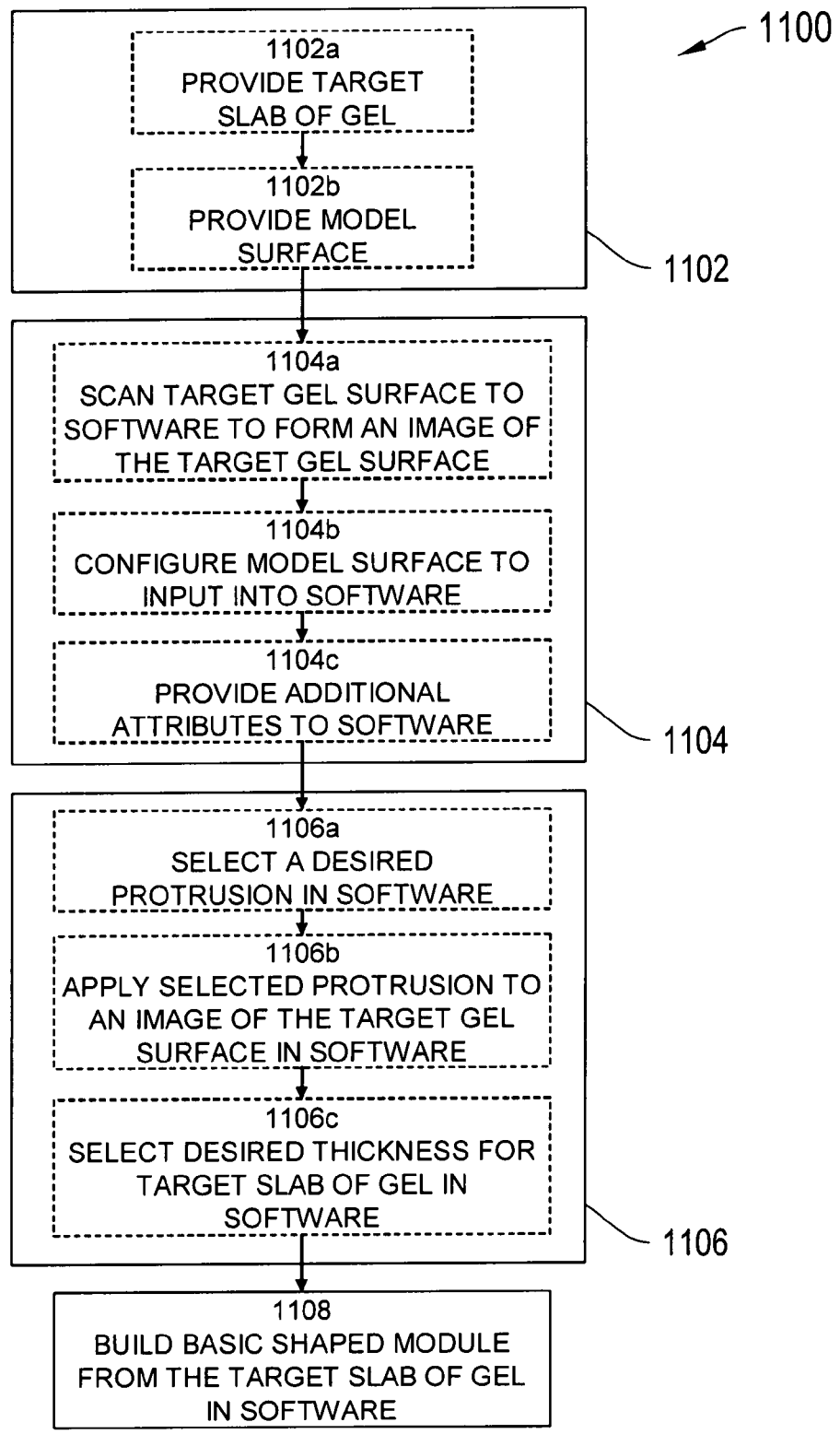
FIG. 11 is a flow chart depicting a method for creating a sensory stimulation apparatus.

FIG. 11 is a flow chart depicting an exemplary method 1100 for creating customized gel modules 100 from injection moldable material. The method 1100 may be implemented by a computer script and may be automated.

Method 1100 begins in a first step by providing a target slab of injection moldable material and a desired model surface (Step 1102 and sub-steps 1102a and 1102b). The target slab may be formed from similar material as described for the gel module 100 of FIG. 1. The target slab of gel may be cut in any desired shape. For example, the target slab of gel may be cut into the shape of a triangle. In another embodiment, the step 1102a includes providing a target mold typically used in an injection molding process.

The desired model surface contains the surface features the user desires to impose at the target slab and may be any surface having a suitable texture. The desired model surface may be a natural object (e.g. tree, rock) or an artificial object (e.g. car, telephone). The desired surface may also be a digital image stored in a computer. The model surface typically includes surfaces that have few, if any, sharp edges which may complicate software rendering (they are points of discontinuity that may result in modeling delays).

In a second step (1104), the user forms a manipulatable electronic image of the target slab and, if not otherwise available, the model surface. The user may also form manipulatable electronic images of the target mold. Such images are stored in a software program that includes a depiction of the target slab of gel and model surface. The software can also be programmed to include surface features, thickness, slope, gel material heat capacity, and other attributes that the user desires to impose on the target slab. Other additional attributes relevant for forming a gel module can be included in the software (step 1104c). These additional attributes may also include protrusions 106 or other shapes formed on target gel surface, and other parameters including the desired number of protrusions 106, the scale and size of protrusions 106, the thickness of the protrusions 106 and thickness of the target gel surface. In one exemplary implementation, the target gel surface is scanned and uploaded into a 3D modeling software (Step 1104a). The attributes of the model surface can also be scanned and uploaded into a 3D modeling software (Step 1104b). In one embodiment, the 3D modeling software used in RHINOceros (RHINO). In other embodiments, the 3D modeling software used in 3D Studio Max, Bryce, Lightwave, Maya, SoftImage and Truespace.

In a third step (1106), the operator customizes a software version of a slab of gel by selecting a desired combination of slab features, and applies the customized features to the target slab (1106).

Exemplary features may be selected (step 1106a) from a group of features which may be modified according to the model surface. For example, a desired surface protrusion pattern 106 may also be selected based on the similarity of features to those of the model. The modified exemplary protrusion 106 may then be applied within the software model so as to appear on the target gel surface (step 1106b). In one embodiment, a plurality of modified protrusions 106 are applied to the electronic image of the target gel surface in the software. In another embodiment, the protrusions 106 are applied as cavities and indentations in the electronic image of the inner surface of the injection mold. In such an embodiment, the intended convex protrusions 106 are first realized as concave cavities in the injection mold which become the convex protrusions 106 when the gel material is poured into the injection mold. A suitable software program may be written to use some of the attributes of the model surface and some additional attributes such as the number of protrusions 106 to determine a desired layout of protrusions 106 on the target gel surface. In one such embodiment, each of the plurality of pattern structures is of differing types, sizes and shapes.

The software may be used to create a thickness for the target slab of gel (step 1106c) based on the thickness attributed entered in step 1104c. In this step, the software may also be used to create a thickness for the injection mold. In one embodiment, the target slab of gel has a uniform thickness. In another embodiment, the target slab of gel has different thicknesses at different locations along the target gel surface. In such embodiments, the additional attributes provide thickness at various locations on the target gel surface. In one embodiment, the step of applying the desired protrusion 106 to the target gel surface (1104b) may be executed after the step of selecting a thickness of the target slab of gel.

In a next step (1108), the operator uses 3D rendering and prototyping to cut, shape and build a target slab of gel comprising a thickness and having a layout of at least one protrusion 106 on the surface. In another embodiment, the operator uses 3D rendering and prototyping to build an injection mold having a desired thickness and a layout of at least one concave cavity corresponding to a protrusion 106. The 3D modeling software may generate an output file in a format suitable for rapid prototyping (for e.g. ".STL") having information about the texture of the target slab of gel. The basic gel module may be constructed using the output file with 3D printers, stereolithography machines or selecting laser sintering systems ("rapid prototyping").

A target gel surface may be shaped as a triangle, rhombus or trapezoid. These shapes may form a group of primary geometric shapes that may be interchangeable. More specifically, two triangles may be combined in a suitable fashion (for example by attaching them along the base) to form a rhombus; three triangles may be combined in a suitable fashion to form a trapezoid. A group of primary geometric-shaped target gel surfaces may be combined in many suitable ways to form hexagonal shapes that conform to the symmetry provided in one or more of the basic geometric shapes. Optionally, the primary geometric shapes may be formed from other shapes without departing from the scope and spirit of the invention. The primary geometric patterns may also be combined in other ways without departing from the scope and spirit of the invention. The assembly of target surfaces to form larger hexagonal patterns may provide for tactile variations and aesthetic appeal. The assembly of target surfaces may serve to form a portion of a puzzle or cognitive developmental exercise that may incorporate both the visual and cognitive stimulus accompanying the solving of a puzzle along with the tactile stimulus provided by the textured gel module.

Exemplary protrusions 106 may include a sphere, hemisphere, cube, cuboid, 3D extensions of other closed form polygons such as pentagons, triangles, water-drop shaped structures. The protrusions 106, alone or in combination, help form the texture of the surface of the target surfaces. The texture may also be based, at least in part, on the variation of the thickness of the target surface. The parameters of the protrusion 106 such as the base area, height or curvature may be selected based on the texture and topology of the external source surface.

As noted earlier, 3D modeling software such as RHINO may be used to model the basic geometric shapes. The textured mold comprising the modeled basic shapes along with a layout of patterns structures may then be built using a 3D printer or other prototyping systems. In one embodiment of the invention, a script may be written which expands on the knowledge gained from modeling the basic shapes and basic protrusions 106 using method 1100 of FIG. 6 to model and build other shapes and surfaces comprising of more complex textures and shapes. In one embodiment, the basic shapes comprising the triangle, rhombus and trapezoid and a group of protrusions 106 may be compared to an alphabet of a language wherein the information from the basic shapes and protrusions is used to generate more complex structures similar to a language where the alphabets may be combined in many different ways to generate more complex words and sentences.

Figure 12:
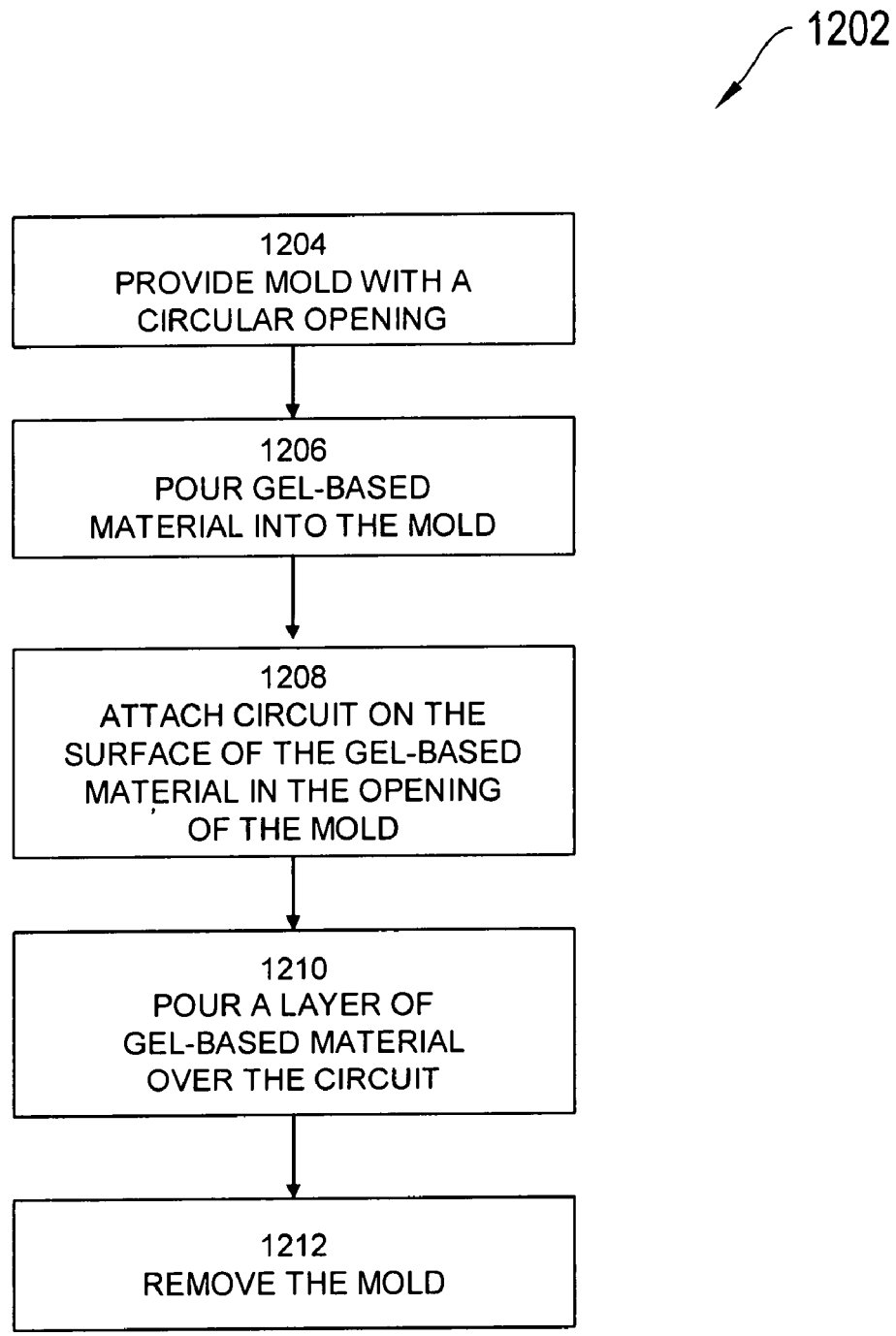
FIG. 12 is a flow chart depicting a method for creating an exemplary textured sensory stimulation apparatus.

Computer-based methods may also be used to manufacture apparatuses 10 having both the gel 100 and a circuit 400 attached to the gel 100. FIG. 12 is a flow chart depicting a process 1202 for creating an exemplary sensory stimulation apparatus 10, according to an illustrative embodiment of the invention. The process 1202 begins with providing a mold with an opening (Step 1204). As noted above, the mold may be sized and shaped to suit a particular application and correspond to a particular module 100. The mold has an opening on a surface, such that a perimeter region of the opening extends above the surface of the mold. The opening serves as a receptacle to receive a circuit 400 and thereby couple the circuit 400 to the module 100 being formed in the mold. As an example, for a sensory stimulation tool similar to apparatus 10, the mold may be a hollow triangular shape having a cavity in its central portion. A surface of the cavity may include topological features such as surface undulations and recesses. In such an example, the opening may be located on a surface different from the surface with the undulations and recesses. The opening may be a circular opening for accommodating a circular shaped circuit (similar to circuit 400) and have a raised perimeter that serves as a confining ledge.

Injection moldable material, such as gel or gel-based material, similar to material 102 is poured into the mold through at least one of the opening or another aperture in the mold (Step 1206). In certain embodiments, gel-based material 102 is poured until the cavity in the mold is substantially filled. In other embodiments, the gel-based material 102 is poured in the mold until level of the gel reaches the lower edge of the opening. In still other embodiments, the gel-based material 102 is poured into the mold until the level of the gel is below the lower edge of the opening.

In the next step 1208, the circuit 400 is applied to the module 100. In certain embodiments, the circuit 400 is attached to a surface of the gel module 100 or it may be embedded within the gel 100. In certain embodiments, the circuit is disposed on the surface of the gel-based material through the opening (Step 1208). The circuit 400 fits within the opening and remains stationary within the walls of the opening. The circuit may be attached to the surface of the gel through an adhesive. Optionally, an additional layer of gel-based material 102 is poured over the circuit 400, thereby embedding the circuit in the gel material 102 (Step 1210). The gel is allowed to set, then the mold is removed (step 1212) to reveal the module 100 having an embedded circuit 400 positioned at a location corresponding to the location of the opening on the mold.

In certain embodiments, the apparatus 10 having gel 100 and circuit 400 is unitarily formed, whereby the components of circuit 400 are integrally combined within the gel-based material during the manufacturing process. In such embodiments, interconnecting conductive wires or thread are suspended in the semi-solid gel-based material and various electronic components including light sources and batteries are placed within the gel-based material and connected to each other through the interconnecting conductive wires or thread. In certain embodiments, various printing techniques are used to apply the circuit 400 directly in the gel-based material including a printing process, screen printing process and decal transfer process.

Figure 13:
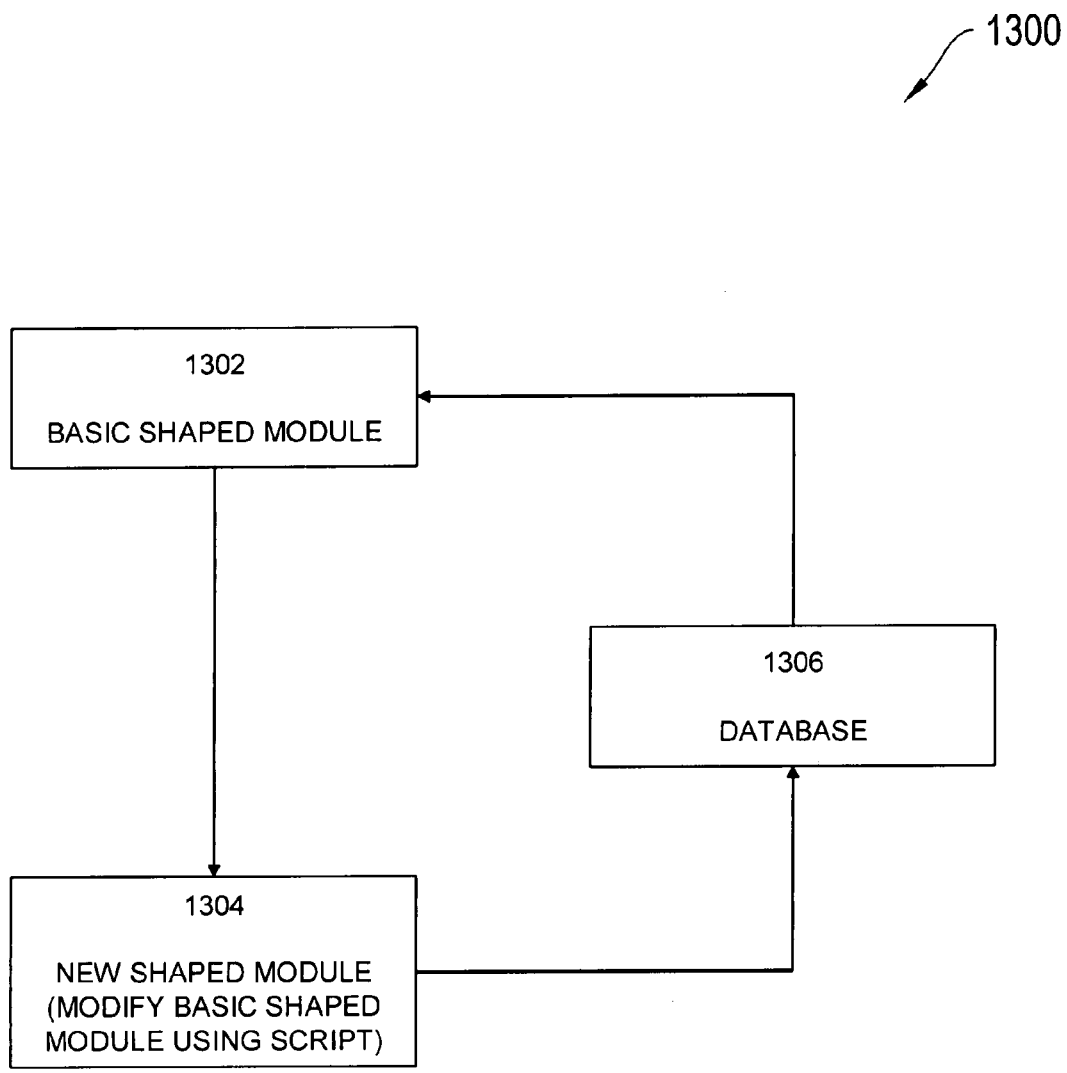
FIG. 13 depicts a process for creating molds for forming sensory stimulation apparatuses having textured surfaces.

FIG. 13 shows a process 1300 whereby the dimensions, surface textures, and other features of an electronic surface formed using the methods described above are measured and stored in a database 1306. These features may be retrieved from the database and used as a script on blueprint of features to be applied to subsequently generated gel modules 1302 to form newly generated surfaces 1304. In one example, the basic gel module 1302 may comprise a simple triangle-shaped gel material and an array of protrusions 106 built on the triangle shaped gel material to form a desired texture 1302. In such an example, the basic gel module 100 has protrusions 106 formed according to the methods shown in FIGS. 11 and 12. In certain embodiments, this basic textured mold may be modified slightly using a script or a computer program to form a large number of textures and shapes 1304. The user may use the script to modify particular characteristics such as protrusion 106 height or slab thickness to create another gel module configured to have a textured surface different from the basic gel module. Some basic characteristics such as the overall triangular shape or design of protrusions 106 may be kept the same as the basic gel module. The changes to the basic gel module 100 result in the formation of different textured surfaces whose attributes may be stored in a computer system and utilized for other more complex gel modules 100. In essence, the images and features configured through the process 1300 may be utilized to generate other shapes without having to start from the beginning. The technique of generating a database of gel modules and protrusions may improve efficiency and enable cost effective prototyping of many different shapes and texture. In another embodiment, process 1300 may also be used to generate a database of injection molds having textured inner surfaces corresponding to the textures of the desired gel module and/or opening for a circuit.

In another embodiment, the script may be used to create textured surfaces in gel type material. Basic textured gel modules may be built comprising basic shapes and protrusions such that the surface texture may be made to match a desired source surface. In one aspect, gel may be used to create soft puzzles and tactile development toys for children such that the textured surfaces combined with the soft feel of the gel to provide a safe and enjoyable educational experience. In one embodiment, a database of shapes, protrusions and corresponding textures may be used such that a desired change in the texture may be provided as an input to the script and a desired textured surface may be provided as an output of the script that may incorporate the desired changes to create a new textured shape. The script modifies the existing textured gel module stored in the database that is most similar in configuration to the desired texture. The script may provide for an automated system to generate new shapes utilizing simple modifications to a known knowledgebase of shapes and textures.

Variations, modifications, and other implementations of what is described may be employed without departing from the spirit and scope of the invention. More specifically, any of the method, system and device features described above or incorporated by reference may be combined with any other suitable method, system or device features disclosed herein or incorporated by reference, and is within the scope of the contemplated inventions. The invention may be embodied in other specific forms without departing from the spirit or essential characteristics thereof. The forgoing embodiments are therefore to be considered in all respects illustrative, rather than limiting of the invention. The teachings of all references cited herein are hereby incorporated by reference in their entirety.

The invention claimed is:

1. A sensory stimulation apparatus, comprising
   an at least partially transparent, pliable gel having an optical property, the gel configured to provide tactile stimulation to the user, and
   a circuit for delivering an electromagnetic radiation to the gel to modify the optical property.
2. The apparatus of claim 1, wherein the circuit is flexible.
3. The apparatus of claim 1, wherein the circuit includes an illuminating layer.
4. The apparatus of claim 3, wherein the illuminating layer includes one or more microscale LEDs.
5. The apparatus of claim 1, comprising a circular printed circuit board having one or more electronic components.
6. The apparatus of claim 1, comprising a layer of gel-based material disposed on the circuit thereby embedding the circuit within the gel.
7. The apparatus of claim 1, wherein the gel and the circuit are attached by an adhesive.
8. The apparatus of claim 1, wherein the circuit is disposed on an exterior surface of the gel.
9. The apparatus of claim 1, wherein the circuit is integrally attached to the gel.
10. The apparatus of claim 1, wherein the circuit is embedded in the gel.
11. The apparatus of claim 10, wherein the circuit is unitarily formed with the gel by dipping the circuit in a gel-based material prior to setting to form the gel.
12. The apparatus of claim 1, comprising at least one interactive layer.
13. The apparatus of claim 12, comprising a processing module for measuring and controlling the operation of the at least one interactive layer.
14. The apparatus of claim 12, wherein the at least one interactive layer includes electronic components.
15. The apparatus of claim 12 wherein the at least one interactive layer comprises a touch sensitive layer.
16. The apparatus of claim 12 wherein the at least one interactive layer comprises a backlight layer.
17. The apparatus of claim 1, comprising a base mat adapted to receive one or more gels.
18. The apparatus of claim 17, wherein the base mat has one or more other circuit elements that interact with the circuit to modify the optical property.
19. The apparatus of claim 17, wherein the base mat includes at least one interactive layer.
20. The apparatus of claim 19 wherein the at least one interactive layer comprises a touch sensitive layer.
21. The apparatus of claim 19 wherein the at least one interactive layer comprises a backlight layer.
22. The apparatus of claim 17, wherein at least one of the gel and base mat includes magnetic elements.
23. The apparatus of claim 17, wherein the base mat is substantially rigid.
24. The apparatus of claim 17, wherein at least one of the base mat and the gel include a coating of at least one of allergen-proof material, mite-proof material, water-proof material and flame-resistant material.
25. The apparatus of claim 17, comprising a plurality of gels adapted to be positioned in a predetermined arrangement on the base mat.
26. The apparatus of claim 17, comprising a case to package the gel and the base mat.
27. The apparatus of claim 1, comprising a plurality of gels adapted to be interfitted with each other to form a unitary pattern.
28. The apparatus of claim 1, comprising a case to package the gel having flat panels that are configured to accept and removably attach to the gels.
29. The apparatus of claim 1, wherein the gel has a textured surface.
30. The apparatus of claim 29 wherein the textured surface further comprises a plurality of protrusions.
31. The apparatus of claim 30 wherein the plurality of protrusions further comprise protrusions of different shapes.
32. The apparatus of claim 29 wherein the gel is formed in a three-dimensional shape.
33. The apparatus of claim 29 wherein the gel has a varied thickness.
34. The apparatus of claim 1, wherein the gel includes a polymeric material.
35. The apparatus of claim 34, wherein the polymeric material includes at least one thermoset elastomer.

36. The apparatus of claim 1, wherein the gel includes at least one smart substance having the optical property.

37. The apparatus of claim 36, wherein at least one of the smart substance includes at least one of a photochromic compound, a halochromic compound, a thermochromic compound and an electrochromic compound.

38. The apparatus of claim 36, wherein the at least one smart substance is about 0.001% to about 0.1% of the gel material on a weight per weight basis.

39. The apparatus of claim 38, wherein the at least one smart substance comprises about 0.001% of the gel material on a weight per weight basis.

40. The apparatus of claim 1, wherein the gel includes at least one of a photochromic compound and luminescent material to provide the optical property.

41. The apparatus of claim 1, wherein the optical property includes at least one of color and brightness.

42. The apparatus of claim 1, wherein the electromagnetic radiation includes waves in the visible spectrum.

43. The apparatus of claim 1, wherein the electromagnetic radiation includes waves in the ultra-violet spectrum.

44. The apparatus of claim 1 wherein the circuit further comprises a plurality of piezo-activated LEDs.

* * * * *